US012697406B2

(12) United States Patent
Ramanand et al.

(10) Patent No.: US 12,697,406 B2
(45) Date of Patent: Aug. 4, 2026

(54) TARGETED SURFACE DISINFECTION SYSTEM WITH PULSED UV LIGHT

(71) Applicant: Solaris Disinfection Inc., Oakville (CA)

(72) Inventors: Prakash Valentino Ramanand, Burlington (CA); Manjinder Singh Dhillon, Milton (CA); Adam Ray Steinhoff, Toronto (CA); Vinod K. Menon, Merrimack, NH (US)

(73) Assignee: Solaris Disinfection Inc., Oakville (CA)

( * ) Notice: Subject to any disclaimer, the term of this patent is extended or adjusted under 35 U.S.C. 154(b) by 477 days.

(21) Appl. No.: 18/143,000

(22) Filed: May 3, 2023

(65) Prior Publication Data

US 2023/0414803 A1 Dec. 28, 2023

Related U.S. Application Data

(63) Continuation of application No. 16/691,019, filed on Nov. 21, 2019, now Pat. No. 11,672,878, which is a
(Continued)

(51) Int. Cl.
*A61L 2/10* (2026.01)
*A61L 2/28* (2006.01)
*A61L 103/75* (2026.01)

(52) U.S. Cl.
CPC .................................... *A61L 2/10* (2013.01); *A61L 2/28* (2013.01); *A61L 2103/75* (2026.01);
(Continued)

(58) Field of Classification Search
CPC .......... A61L 2/10; A61L 2/28; A61L 2202/11; A61L 2202/14; A61L 2202/16; A61L 2202/25
See application file for complete search history.

(56) References Cited

U.S. PATENT DOCUMENTS 4,981,651 A * 1/1991 Horng ........................ A61L 2/10
34/104
8,907,304 B2 12/2014 Kreitenberg
(Continued)

FOREIGN PATENT DOCUMENTS

CA 2511277 C * 8/2016 ............. H05B 47/20

*Primary Examiner* — Regina M Yoo
(74) *Attorney, Agent, or Firm* — Kevin J Fournier IP Legal Services Ltd; Kevin J Fournier

(57) ABSTRACT

Embodiments of a targeted surface disinfection system are disclosed. The system includes a set of one or more UV lamps, a high voltage power supply for driving the lamps, a mobile carriage including a chassis supporting the set, an articulated head assembly including at least one UV lamp from the set, a vacuum pump, and a suction hose extending between the vacuum pump and the head assembly for dissipating heat generated by the at least one UV lamp. The system also includes a pulse configuration control unit for configuring an output of the high voltage power supply for driving the set to emit a UV radiant energy upon a target surface requiring disinfection, where the set of one or more UV lamps emits the UV radiant energy at a rate of at least 20 pulses per second.

19 Claims, 19 Drawing Sheets

Related U.S. Application Data continuation-in-part of application No. 15/095,212, filed on Apr. 11, 2016, now Pat. No. 10,485,887.

(60) Provisional application No. 62/146,299, filed on Apr. 12, 2015.

(52) U.S. Cl.
CPC ........ *A61L 2202/11* (2013.01); *A61L 2202/14* (2013.01); *A61L 2202/16* (2013.01)

(56) References Cited

U.S. PATENT DOCUMENTS

| | | | |
|---|---|---|---|
| 9,165,756 B2 | 10/2015 | Stibich et al. | |
| 2004/0028553 A1 | 2/2004 | Panico | |
| 2006/0219937 A1* | 10/2006 | Henry .................. | G01N 21/658 |
| | | | 250/425 |
| 2007/0187612 A1* | 8/2007 | Inoue .................. | B29C 65/1435 |
| | | | 250/372 |
| 2007/0290621 A1* | 12/2007 | Clark ...................... | F21V 29/74 |
| | | | 315/112 |
| 2008/0032252 A1* | 2/2008 | Hayman .............. | A61B 5/0088 |
| | | | 433/29 |
| 2008/0056933 A1 | 3/2008 | Moore | |
| 2009/0191100 A1 | 7/2009 | Deal | |
| 2011/0305597 A1 | 12/2011 | Farren | |
| 2012/0313014 A1* | 12/2012 | Stibich ...................... | A61L 2/10 |
| | | | 250/492.1 |
| 2013/0002445 A1 | 1/2013 | Stibich et al. | |
| 2013/0330235 A1* | 12/2013 | Stibich ...................... | A61L 2/24 |
| | | | 422/292 |
| 2014/0001374 A1* | 1/2014 | Ullman .................. | A61L 9/205 |
| | | | 250/492.1 |
| 2015/0086420 A1 | 3/2015 | Trapani | |
| 2015/0190538 A1* | 7/2015 | Olvera ...................... | A61L 2/24 |
| | | | 250/455.11 |

* cited by examiner

TARGETED SURFACE DISINFECTION SYSTEM WITH PULSED UV LIGHT

RELATED APPLICATION

The present application is a continuation application of U.S. patent application Ser. No. 16/691,019, filed Nov. 21, 2019, now U.S. Pat. No. 11,672,878 issued on Jun. 13, 2023, which is a continuation-in-part application of the U.S. patent application Ser. No. 15/095,212 filed on Apr. 11, 2016, now U.S. Pat. No. 10,485,887 issued on Nov. 26, 2019, which claims the priority benefit of U.S. Provisional Application No. 62/146,299, filed Apr. 12, 2015, the entirety of which is incorporated herein by reference.

BACKGROUND OF THE INVENTION

1. Technical Field

The present invention relates generally to systems and methods for disinfection and decontamination of surfaces and, in particular, to systems and methods which employ pulses of Ultra Violet (UV) light for surface disinfection and decontamination.

2. Antecedents of the Invention

UV radiation has been employed for disinfection and decontamination of surfaces, air, and liquids. It is considered to be one of the best non-contact decontamination processes. The UV-C region of the UV spectrum has been found to be the most lethal to microorganisms; the strongest germicidal effects have been reported to be in the wave-length from 200 nm to 280 nm. This part of the spectrum has been found lethal to several ranges of microorganisms.

Traditionally, UV radiation for disinfection employed medium pressure mercury vapor lamps to generate UV radiation. In recent decades, pulsed xenon lamps have been found to be much more effective than other UV light emitting technology.

There are several reasons which play a critical role in the efficacy of pulsed xenon UV radiation used for disinfection. One is the broadband spectrum of UV discharge in xenon lamps.

Another reason is that pulsed xenon UV systems have the capability of discharging several megawatts of UV energy in micro-seconds or milliseconds, causing irreversible changes in the cellular level in the microorganisms exposed. Pulsed xenon UV light technology was first developed in Japan. In 1984 Hiramoto patented pulsed UV light technology for sterilization applications. Since then it has been employed for various applications involving disinfection and decontamination.

The spectral output of a UV xenon lamp is very similar to that of sunlight. It goes from 180 nm to 1100 nm, with some major spikes in visible region of the spectrum. The xenon UV discharge lamp can be designed in different geometries to best fit the application. That makes the pulsed UV system very flexible. The system can be tailored to best fit the application in terms of energy requirement.

The energy dissipated can be controlled in terms of number of pulses, energy per pulse, and pulse width. Since the xenon UV flash tube discharges in pulses, the existing systems are not a good fit for applications involving fast moving targets.

Characteristics of Pulsed UV Light Relevant to Disinfection

Pulsed light energy is typically measured in fluence and is related to fluence rate. Fluence rate is the total radiant energy falling on a small transparent sphere containing a target from all possible directions, divided by a cross section of the target. It is generally expressed in W/m$^2$.

Fluence can be defined as the product of fluence rate, exposure time in seconds and a total amount of energy incident on the target during the exposure time. It is expressed in J/m$^2$ or J/cm$^2$.

$$F=e*t*f$$

Where F is the fluence (J/cm$^2$), "e" is the energy per pulse (J/cm$^2$/pulse). "t" is the time in seconds, and "f" is the frequency.

A well-known general rule in photochemistry, the Bunsen-Roscoe reciprocity law, states that the extent of photochemical effects on living beings is determined by cumulative irradiance. Accordingly, for disinfection applications, the current methods and apparatuses using pulsed UV light technology tend to employ high UV energy per pulse, and relatively low frequencies of 1-2 pulses per second.

Typical prior art systems employing pulsed xenon UV lamps for disinfection are disclosed in U.S. Pat. Nos. 9,093,258, 8,872,669 and 9,165,756 as well as U.S. Patent Application Publication No. 2013-0330235. These systems suffered from various shortcomings, however.

They employed a lower pulse frequency (typically below 2 Hz), therefore took longer time to inactivate germs. They employed a high discharge energy per pulse (typically more than 500 joules), therefore the generated noise level was high (manifested as loud popping sounds) causing disturbance around the treated area. The high energy of discharge also generated an unsafe amount of ozone, which had to be removed by specialized fans and filters, contributing to additional cost, complexity, and noise. They employed a 360-degree, all around flashing UV light geometry for entire room disinfection, thereby wasting energy if only certain limited surfaces were in need of treatment. To compensate for the wasted energy, they required a longer operating time in each room, hence, a relatively high overall energy consumption. Due to their high level of ozone generation, they required additional filtration and power consuming auxiliary components such as blower motors, etc., which resulted in higher energy consumption per unit time. They employed optical filters (to filter out the visible light produced by the lamps), which did not fully eliminate visible pulsating light while decreasing the UV capability of the apparatus.

SUMMARY OF THE INVENTION

The present invention responds to an unmet need for systems and methods that do not suffer from the shortcomings of the antecedents referenced above. Embodiments of the present invention provide improved systems and methods which enable targeted surface decontamination and room disinfection capabilities, operate rapidly, focus more effectively only on targeted contaminated surfaces, and are more energy efficient. One embodiment of the present invention includes a mobile pulsed xenon UV disinfection unit including an articulated lamp or head assembly carrying a UV lamp, an additional lamp assembly including a second UV lamp, a detachable lamp assembly, a third UV lamp, and one or more removable lamps, and a set of corresponding parabolic reflectors. The pulsed xenon UV disinfection unit further includes a high voltage power supply and a pulse configuration control unit, which may be mounted in a chassis.

The chassis may be seated on a robotic mobile carriage or platform and housed within a cabinet. Embodiments may include the pulse configuration control unit being programmed to drive a set of the xenon UV lamp, the second UV lamp, the third UV lamp, and/or the one or more removable lamps to emit UV pulses having a predetermined energy, e.g., 30-150 joules of energy per pulse, at a preset frequency, or pulse rate, within a predefined frequency range, e.g., 20-50 Hz. In one example, the pulse rate may range from 25 to 35 Hz. Various software and hardware components may be included to achieve an additional functionality such as remote video imaging of a target area, remote control of the mobile carriage or platform, an articulated movement of the lamp or head assembly, inward and outward orientations of the lamp assembly or a component thereof such as a UV lamp and/or a lamp housing, a safety emergency shutoff, remote management, reporting, data storage, billing, etc.

From the foregoing compendium, it will be appreciated that a feature of the present invention is to provide a targeted surface disinfection system with pulsed UV light of a general character not being subject to the disadvantages of the aforementioned antecedents of the present invention.

An aspect of the present invention is to provide a targeted surface disinfection system with pulsed UV light of a general character using a higher frequency pulsing rate relative to those used with the aforementioned antecedents for more effective bombardment of microorganisms.

A consideration of the present invention is to provide a targeted surface disinfection system with pulsed UV light of a general character which uses a lower discharge energy per pulse relative to those used with the aforementioned antecedents, and hence, generates lower noise and low ozone to the point where additional ozone filters may not be required.

A further feature of the present invention is to provide a targeted surface disinfection system with pulsed UV light a general character which allows the targeted disinfection of just the desired surfaces and areas of a room, with capability for precise control of the amount of UV light that hits each targeted area, and hence it does not waste energy by irradiating non-target areas.

Another aspect of the present invention is to provide a targeted surface disinfection system with pulsed UV light of a general character which requires less time per average room for targeted disinfection, therefore it has a lower energy consumption which reduces its cost of operation.

A further consideration of the present invention is to provide a targeted surface disinfection system with pulsed UV light of a general character where a higher percentage of power used is converted into useful UV energy being emitted on to the targeted surfaces.

A still further aspect of the present invention is to provide a targeted surface disinfection system with pulsed UV light of a general character which does not require additional optical filters or ozone filters.

BRIEF DESCRIPTION OF THE DRAWINGS

In the accompanying drawings, in which are shown an exemplary embodiment of the present invention.

4

Figure 1:
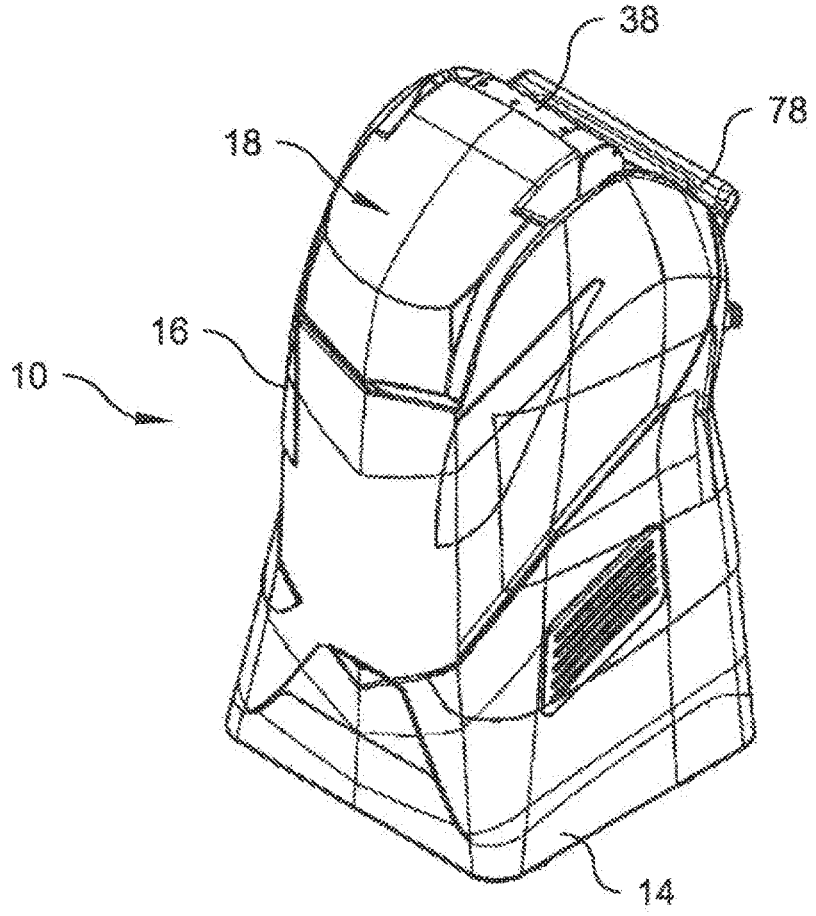
FIG. 1 is an isometric view of a targeted surface disinfection system in accordance with an embodiment of the present invention illustrating a cabinet housing a chassis and with an articulated lamp or head assembly in a retracted position.
Figure 2:
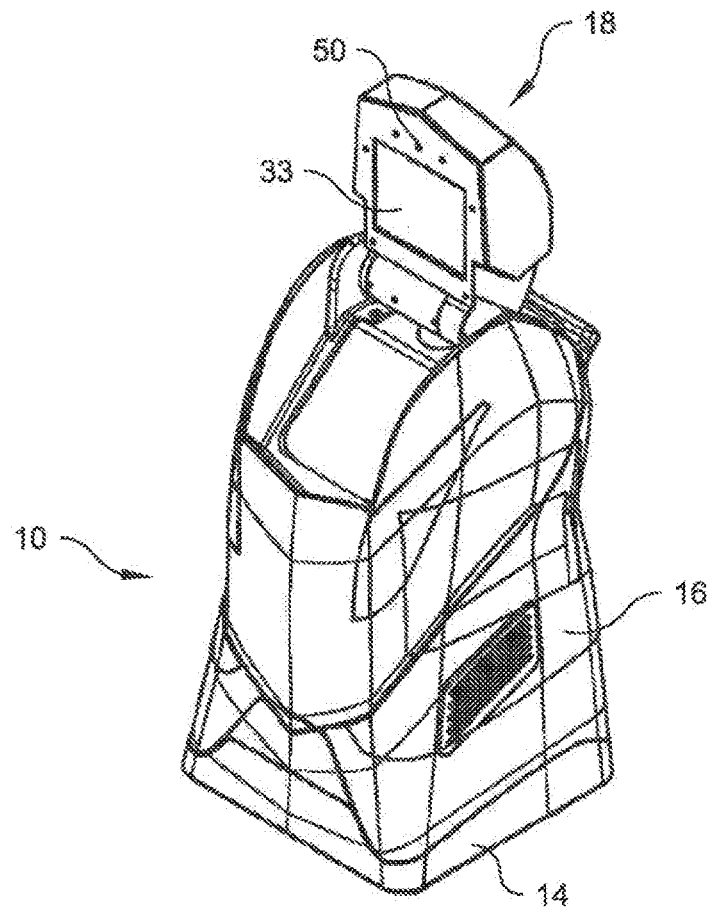
Figure 3:
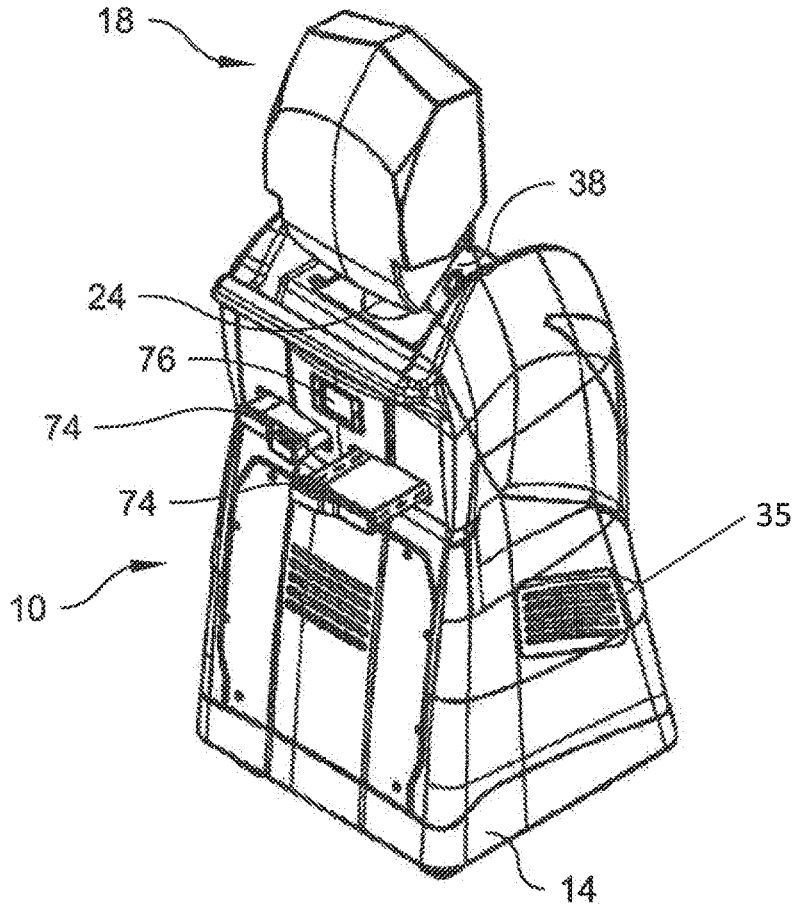
Figure 4:
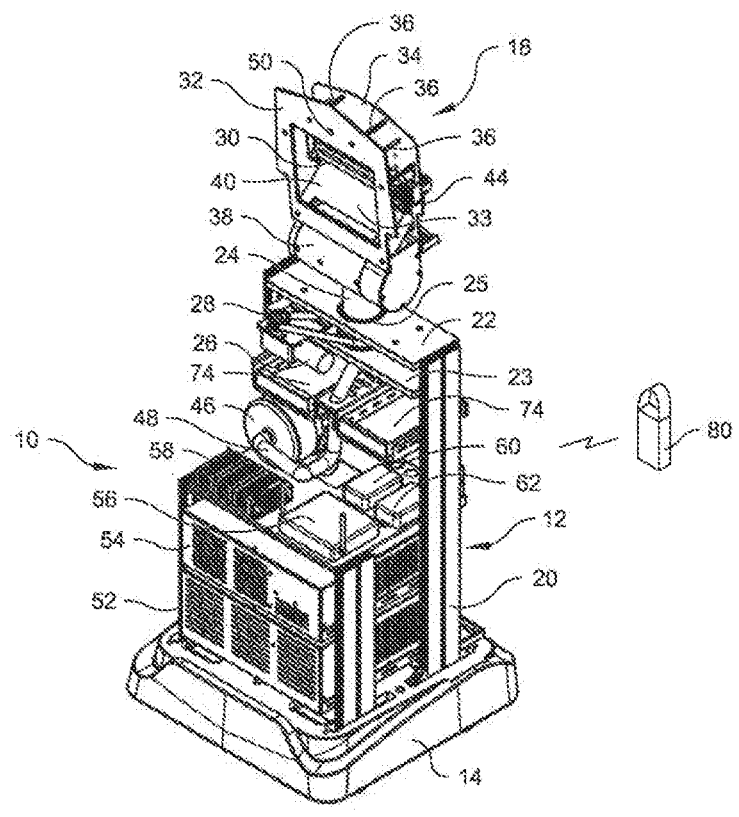
Figure 5:
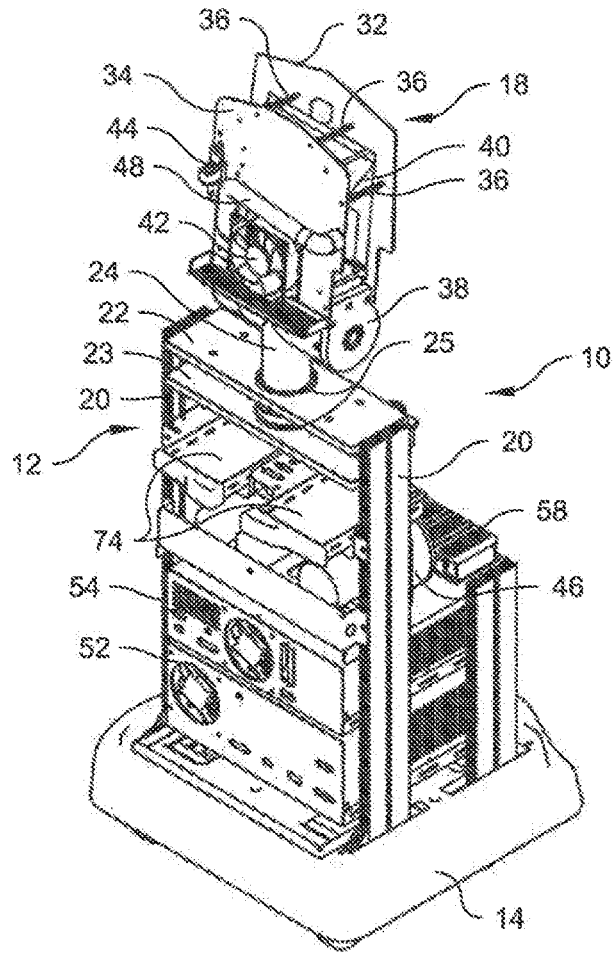
Figure 6:
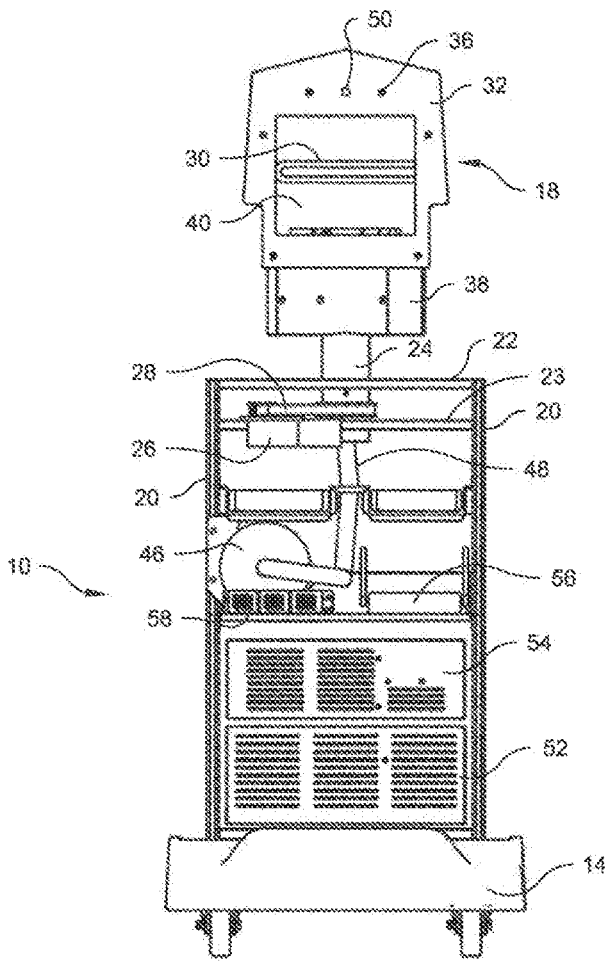
Figure 7A:
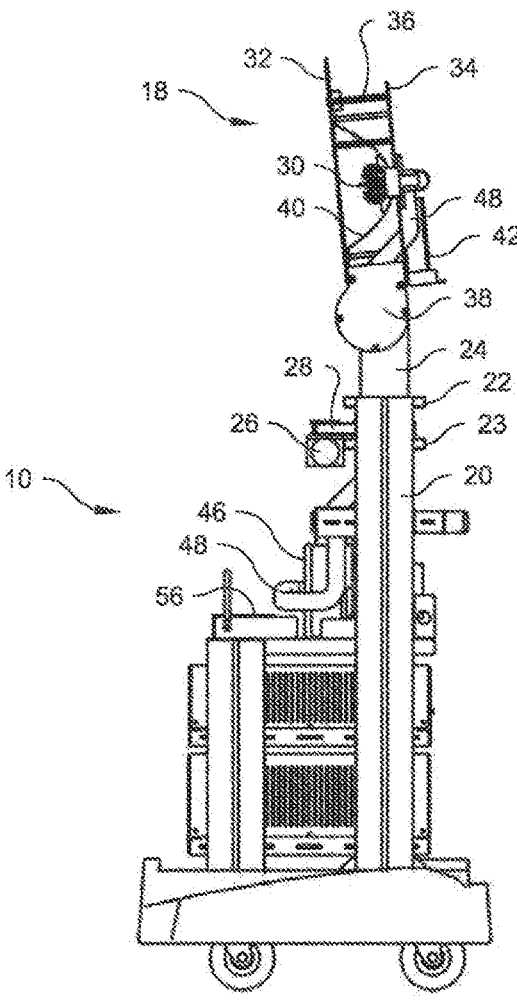
Figure 7B:
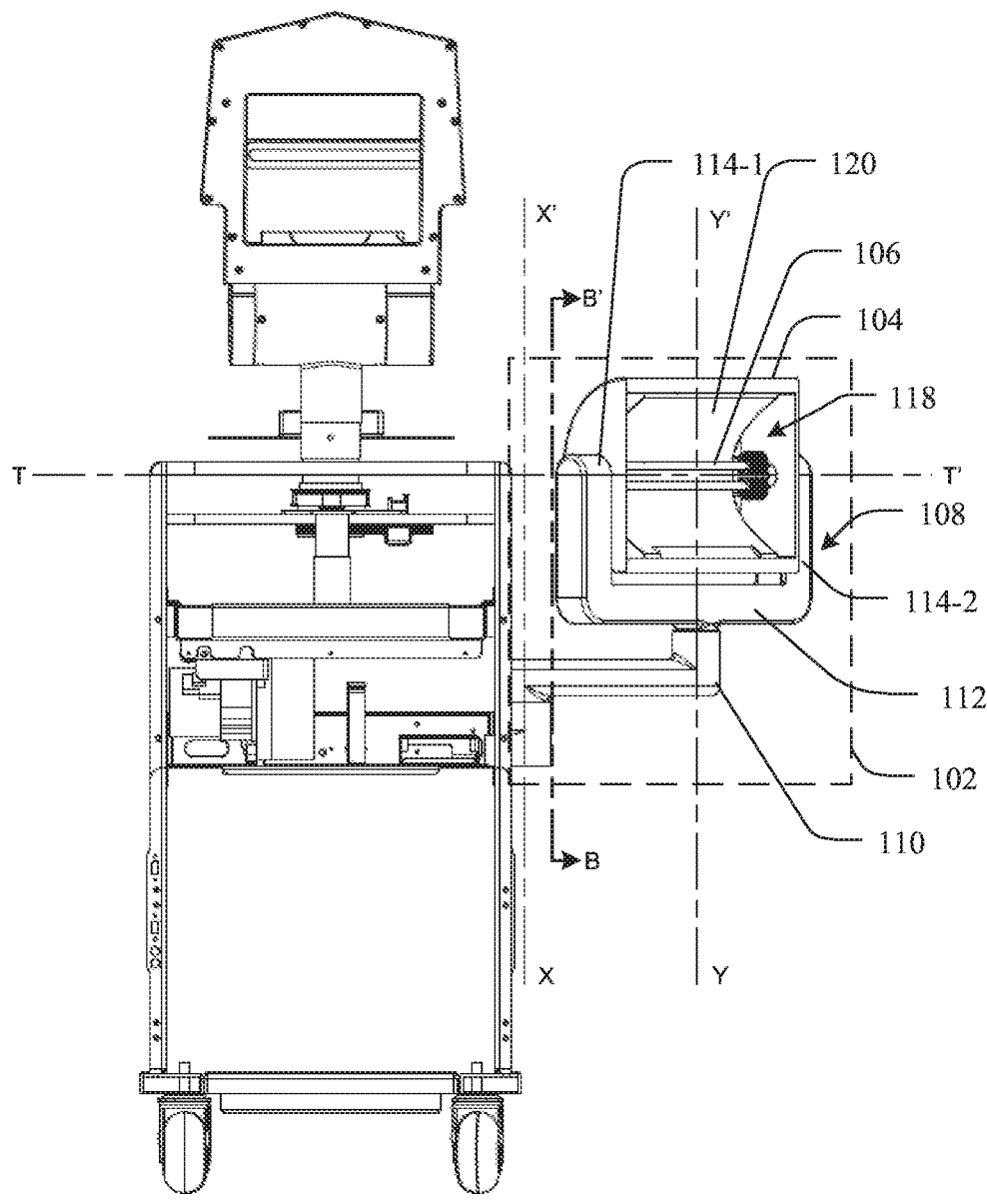
Figure 7C:
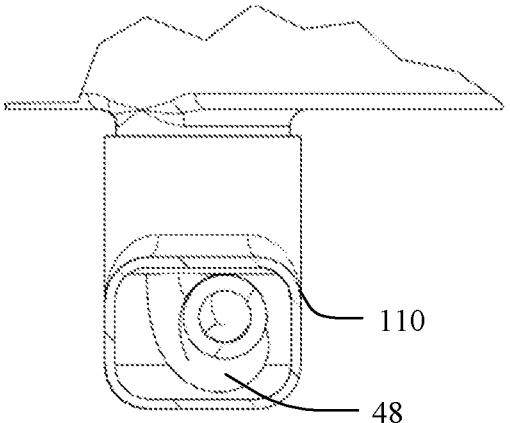
Figure 7D:
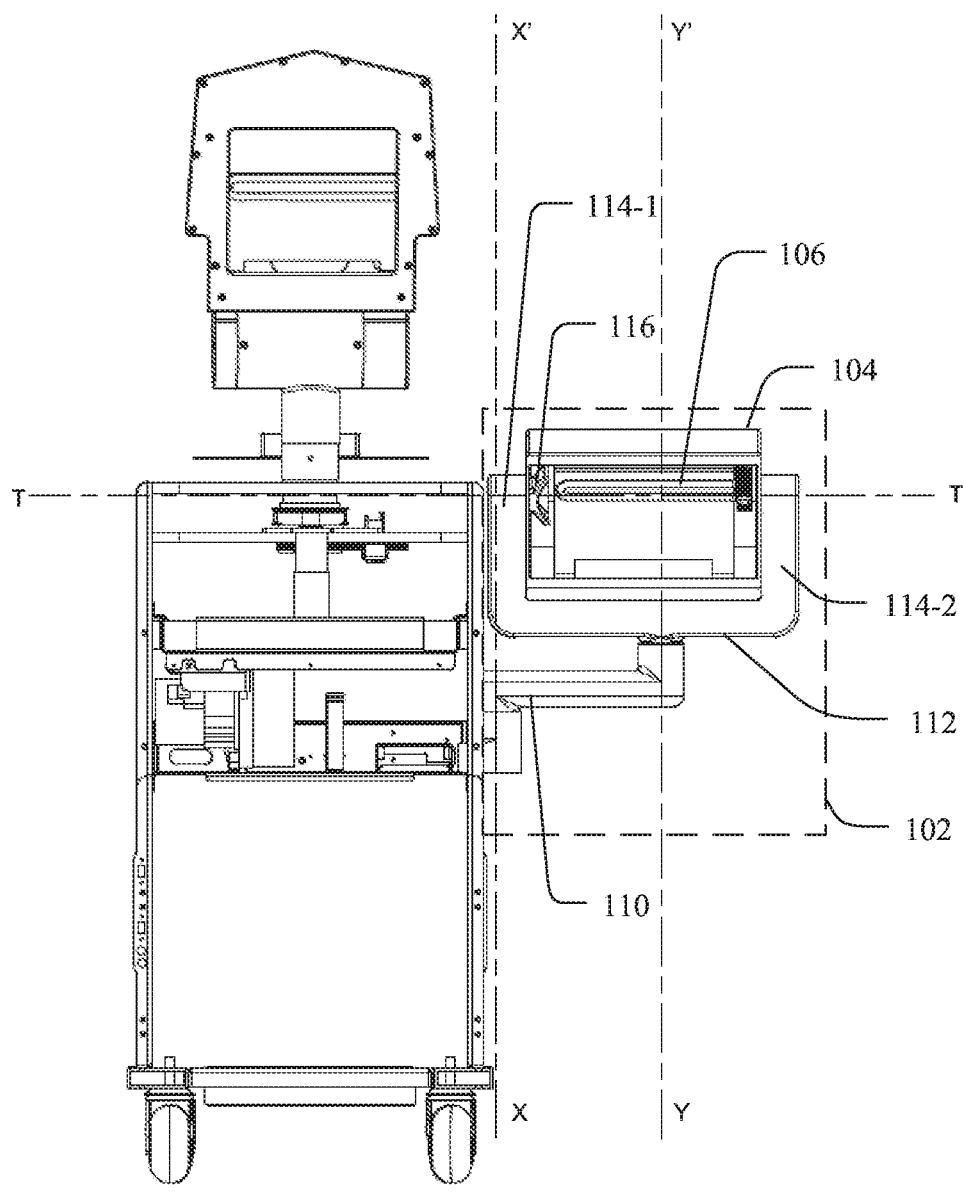
Figure 7E:
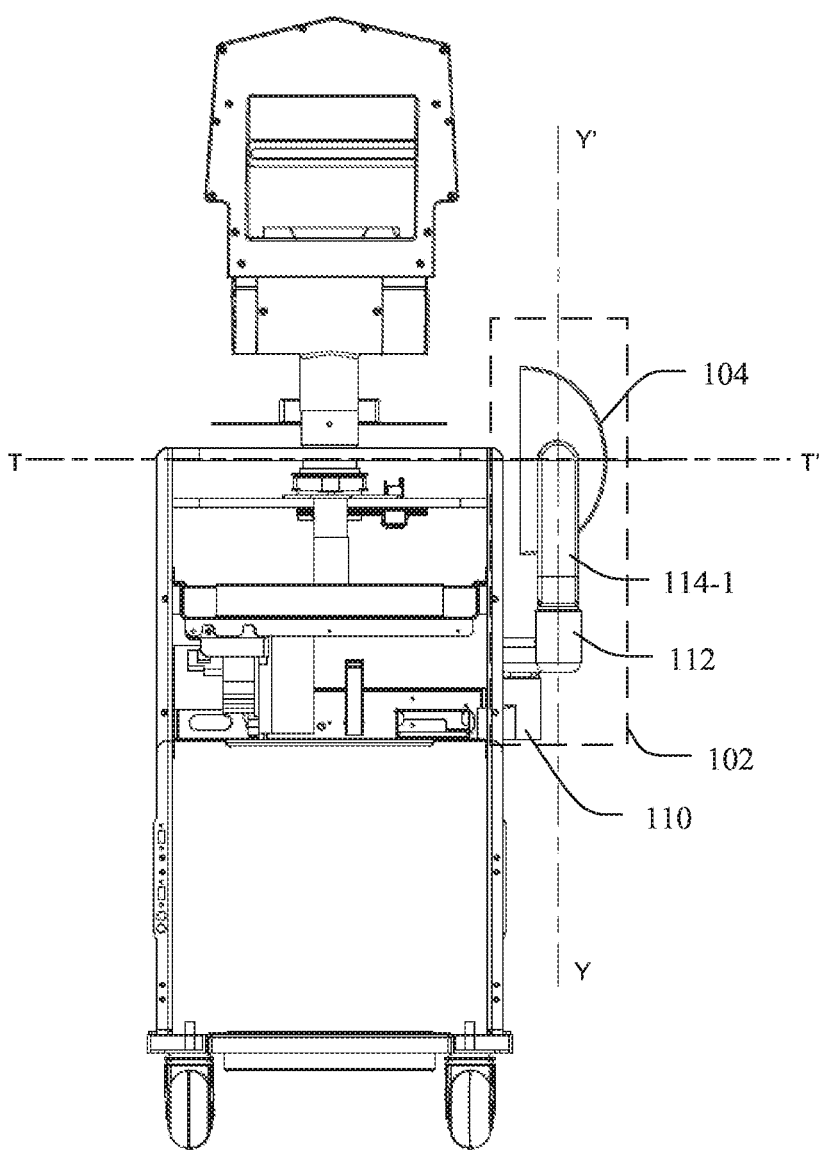
Figure 7F:
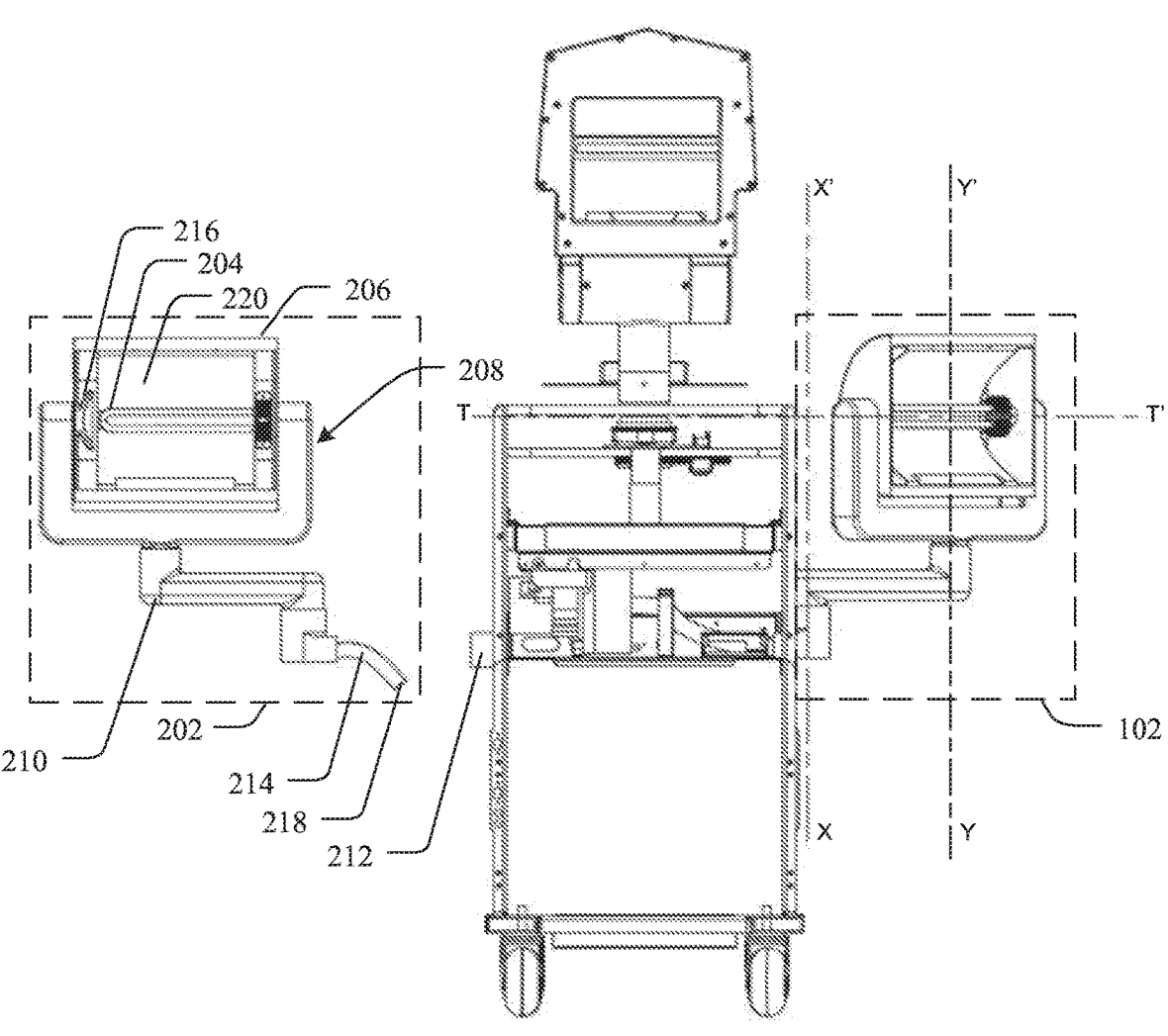
Figure 8:
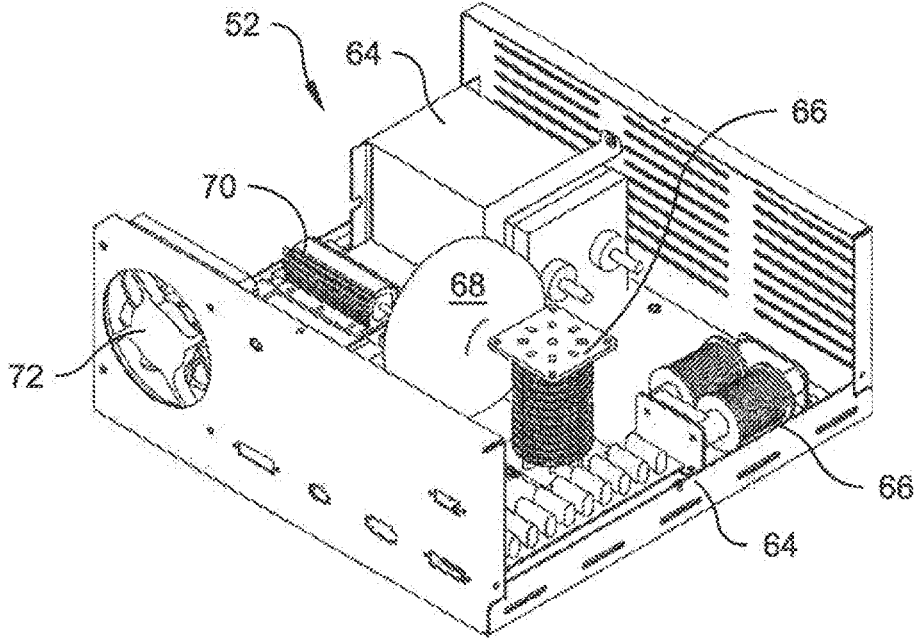
Figures 9A, 9B:
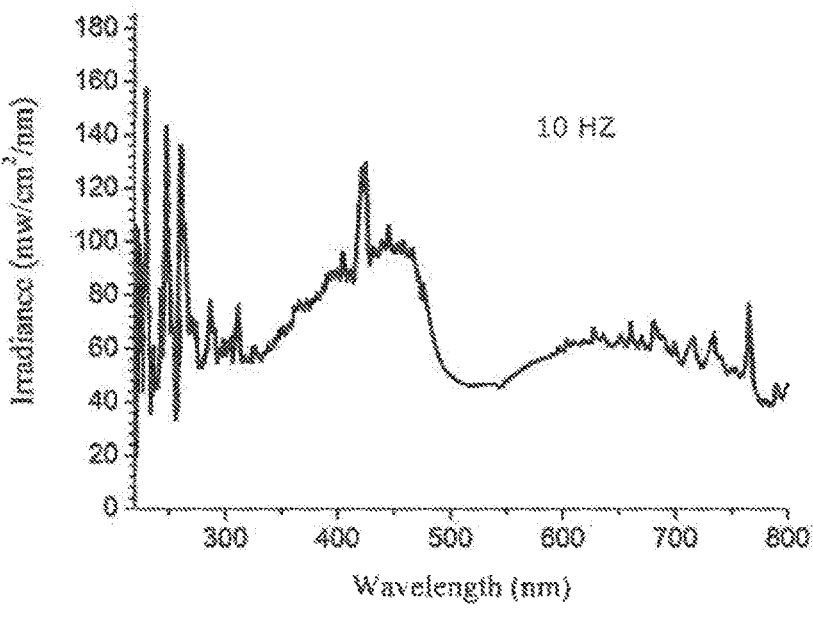
Figure 9C:
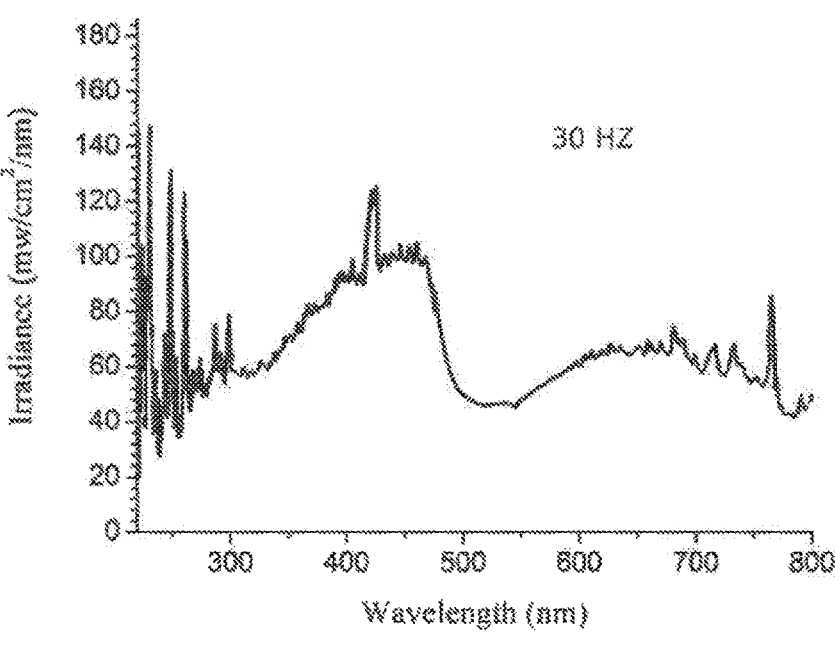
Figure 9D:
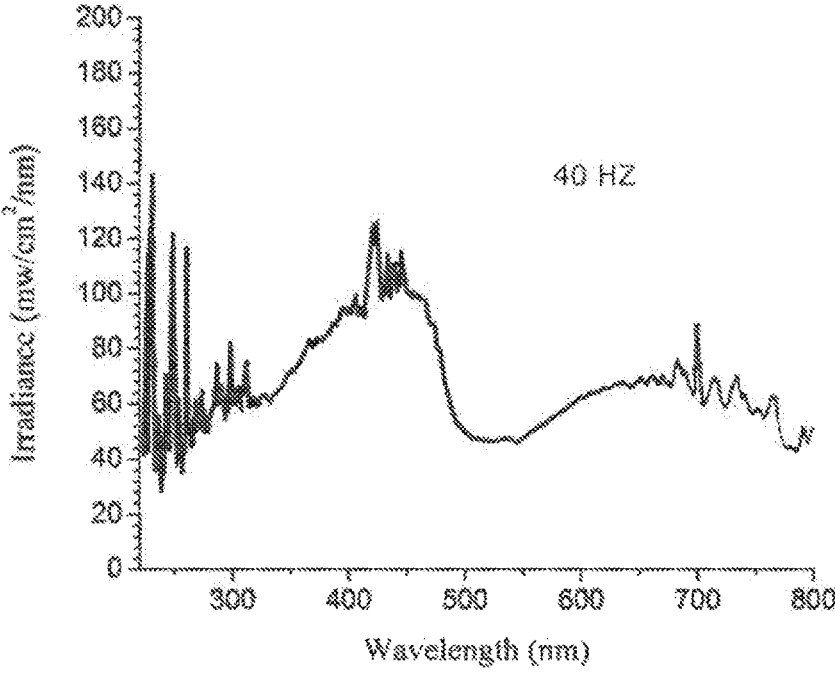
Figure 9E:
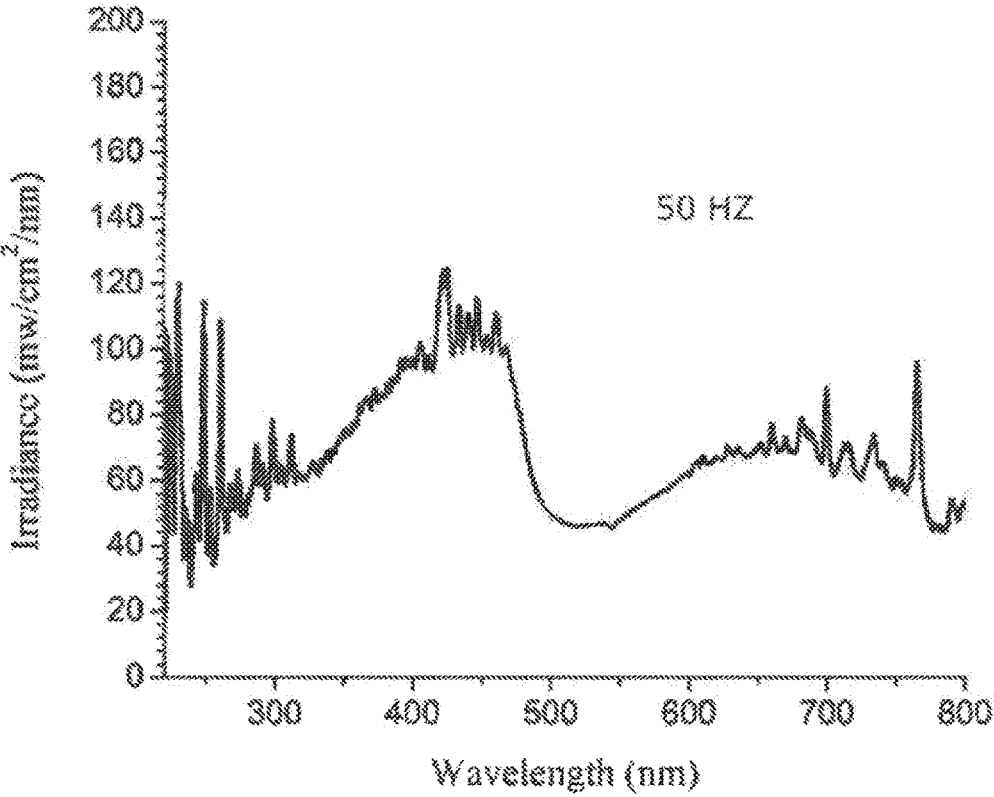
Figure 10:
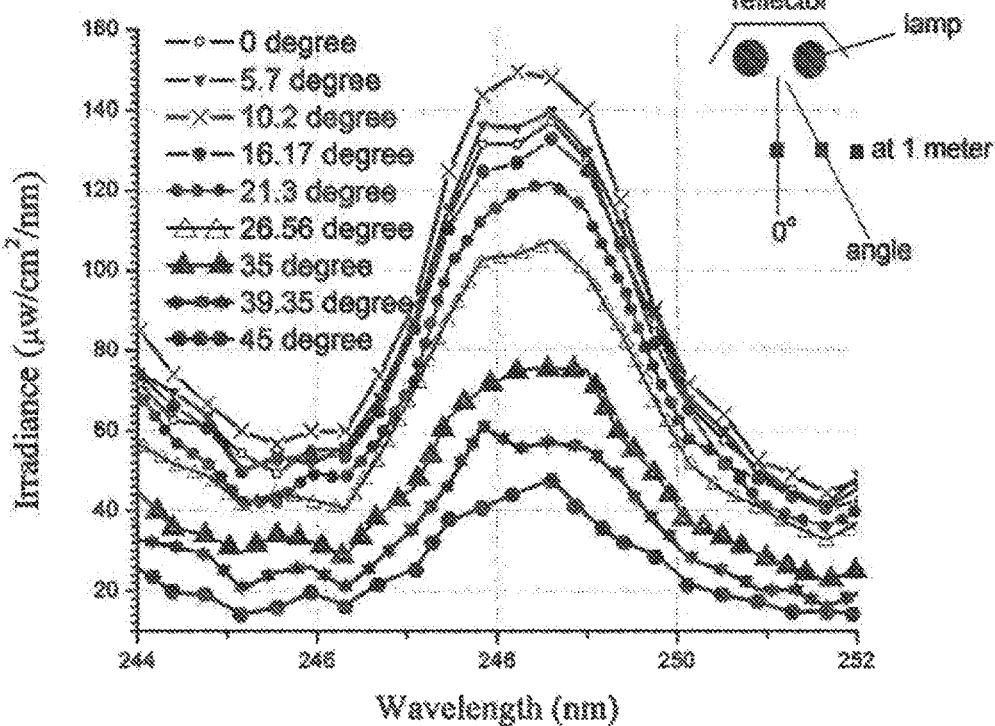
Figure 11A:
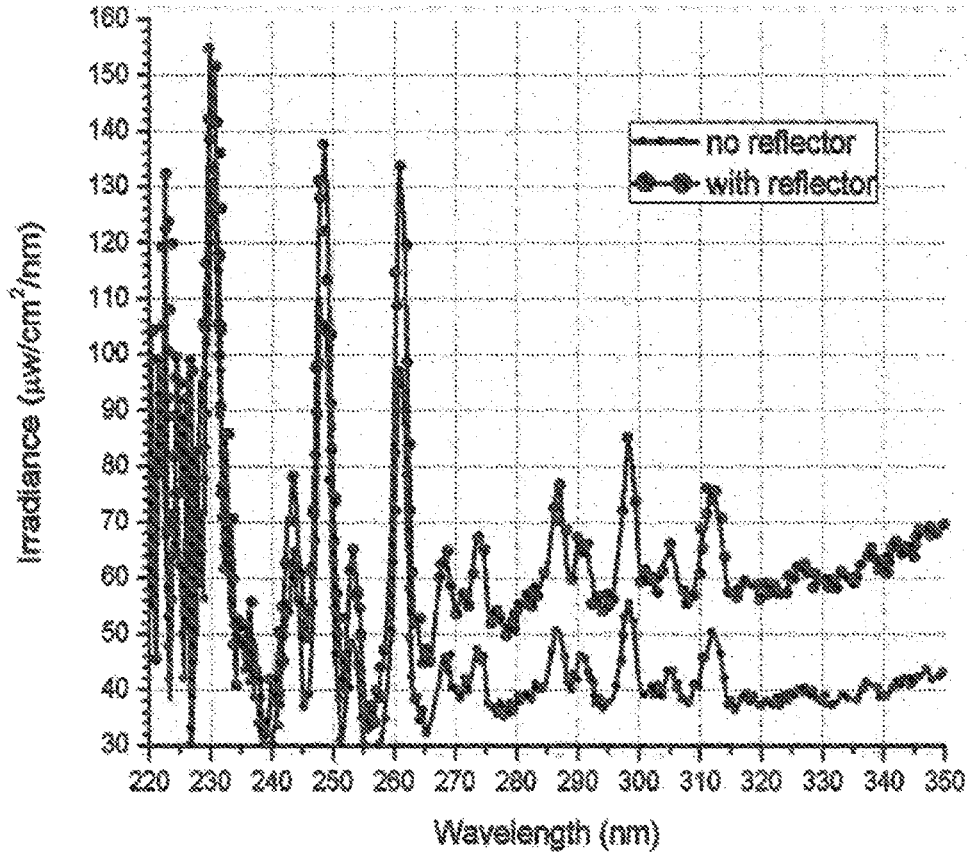
Figure 11B:
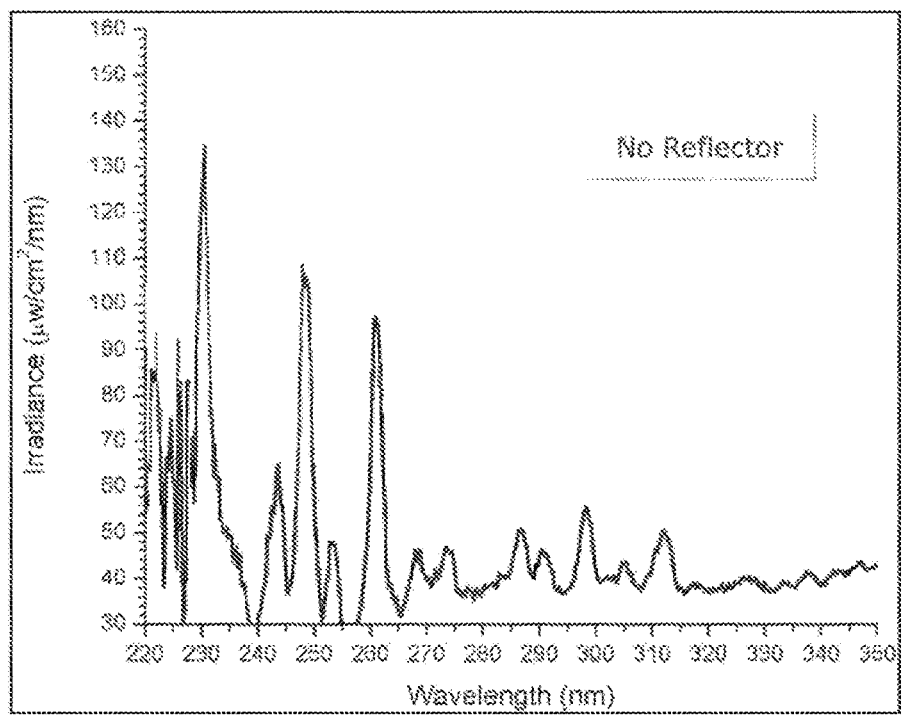
Figure 11B:
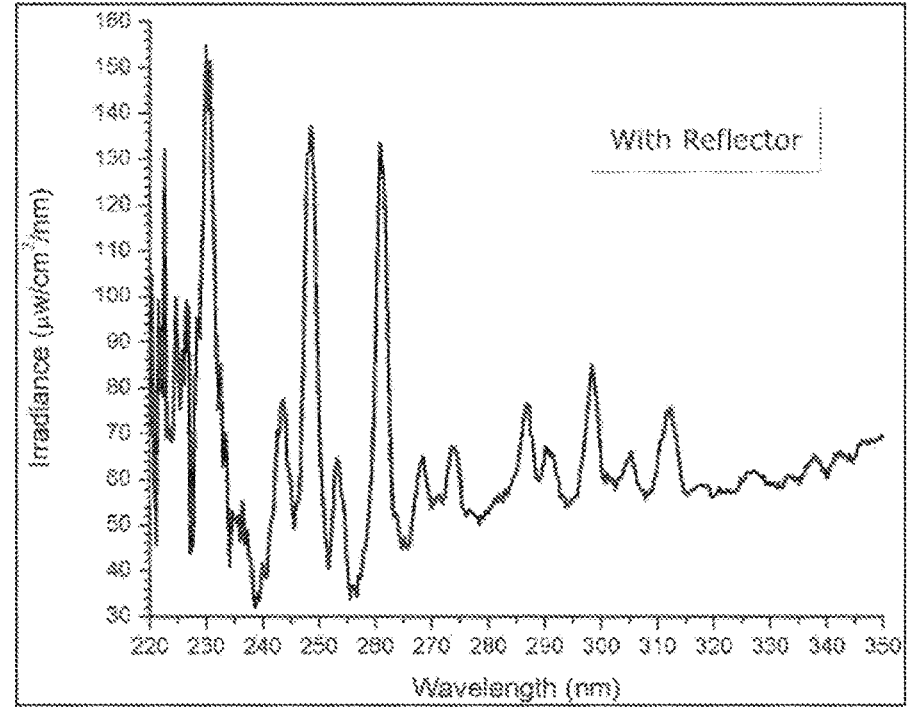

FIG. 2 is an isometric view of the targeted surface disinfection system, similar to FIG. 1, but showing the head assembly in an operative position:

FIG. 3 is a rear isometric view of the targeted surface disinfection system of FIG. 1 with the head assembly in an operative position;

FIG. 4 is an isometric view similar to FIG. 2, but with the cabinet removed;

FIG. 5 is a rear isometric view similar to FIG. 3 with the cabinet removed;

FIG. 6 is a rear elevational view of the targeted surface disinfection system of FIG. 1 with the cabinet removed;

FIG. 7a is a side elevational view of the targeted surface disinfection system of FIG. 1 with the cabinet removed:

FIG. 7b is a front elevation view of the targeted surface disinfection system illustrating an exemplary additional lamp assembly according to another embodiment of the present invention;

FIG. 7c is an enlarged scale sectional view taken along the plane B-B of FIG. 7b;

FIG. 7d is an illustration showing the exemplary additional lamp assembly of FIG. 7b in an alternate orientation;

FIG. 7e is an illustration showing the additional lamp assembly in a different orientation;

FIG. 7f is a front elevation view of the targeted surface disinfection system illustrating an exemplary detachable lamp assembly according to yet another embodiment of the present invention;

FIG. 8 is an isometric view of a high voltage power supply, with portions of its cabinet removed to better illustrate exemplary components thereof;

FIGS. 9a-9e are a set of a graphs of test results indicating xenon lamp energy output at different pulse rates;

FIG. 10 is a graph of test results indicating xenon lamp energy output variance as a function of incident angles; and FIGS. 11A and 11B comprises a set of graphs of test results indicating xenon lamp energy output with and without a reflector.

DETAILED DESCRIPTION

Embodiments of the present invention will now be described in detail with reference to the drawings, which are provided as illustrative examples so as to enable those skilled in the art to practice the disclosed or related embodiments. Notably, the figures and examples below are not meant to limit the scope of the present invention to a single embodiment, but other embodiments are possible by way of interchange of some or all of the described or illustrated elements.

Moreover, where certain elements of the present invention can be partially or fully implemented using known components, only those portions of such known components that may be necessary for an understanding of the present invention will be described, and detailed descriptions of other portions of such known components will be omitted so as not to obscure the potential embodiments. In the present specification, an embodiment showing a singular component should not be considered limiting; rather, the present invention is intended to encompass other embodiments including a plurality of the same components, and vice-versa, unless explicitly stated otherwise herein.

Moreover, any term in the specification or claims is not intended to be ascribed an uncommon or special meaning unless explicitly set forth as such. Further, the present invention encompasses present and future known equivalents to the known components referred to herein by way of illustrations.

With reference now to the drawings, wherein like numerals refer to like components throughout, the reference numeral 10 denotes generally a targeted surface disinfection unit with pulsed UV light constructed in accordance with embodiments of the present invention. Further, the term "targeted surface disinfection system" is used in the present invention in the context of its broadest definition. The targeted surface disinfection system may refer to a stand-alone or a networked electronic or electromechanical device capable of providing a germicidal agent for disinfection. In one embodiment, the targeted surface disinfection system may refer to a disinfection apparatus (e.g., the targeted surface disinfection unit 10) configured to provide the pulsed UV light of a predetermined frequency suitable for deactivating or killing an intended pathogen. Some embodiments may further include such disinfection apparatus being configured to operate independently or in communication with a set of one or more devices including, but not limited to, (i) sensors (e.g., motion sensors, proximity sensors, temperature sensors, light sensors, sound sensors, pathogen detection sensors, pathogen identification sensors, electrical parameter sensors such as voltage sensors, current sensors, power sensors, dose/dosage sensors, and intensity sensors, etc.), (ii) remote control systems (e.g., wired or wireless devices, portable or fixed devices, dedicated or smart devices, generic or application-specific devices, scanners or readers, servers or client devices, automated or non-automated, machine-controlled or user controlled devices, single-use or multi-use devices, etc.), (iii) another disinfection apparatus (e.g., a light-based disinfection apparatus, a chemical disinfection apparatus, a sound or vibration-based disinfection apparatus, liquid or vapour-based disinfection apparatus, etc.), (iv) robotic or non-robotic devices and/or any components (including implementing or supporting computer programs) connected or supported therewith.

Embodiments of the targeted surface disinfection system may include the targeted surface disinfection unit 10 ("the unit 10") for targeted surface disinfection. The unit 10 may include a chassis 12, mounted on a remote controlled robotic mobile carriage (or platform) 14 is enclosed in a cabinet 16. The cabinet 16 may be fabricated out of a fire-retardant polymer, but any other suitable materials known in the art, related art, or developed later can be employed. The mobile carriage or platform 14 is fitted with electric motors connected to floor mobility devices, e.g., wheels, tracks, mecanum wheels, casters, traction wheels, omnidirectional wheels, etc., which allow the entire unit 10 to move (e.g., sideways, forward, rotate, backward, etc.) and to be relocated with precision to any desired target position in a room or proximate to a target surface, allowing navigation around furniture and in tight spaces/corners. Optionally, the wheels can be omnidirectional, for example, allowing the unit 10, or a component thereof, to move to the sides while facing forward, for instance, relative to (i) an aspect of the unit 10, (ii) a spatial position or an orientation of such aspect, (iii) a person or an object proximate to the unit 10, (iv) a target surface or a portion/region/object proximate thereto, (v) a signal or feedback (e.g., audio, visual, light, haptic, vibrational, radiofrequency, etc.) being received from a signal source. Examples of the aspect may include, but are not limited to, a surface (e.g., an outer surface or an inner surface of the unit 10 or a component thereof), a side (e.g., a side proximate to or along a UV lamp, a side away from a user, a side oriented towards a target surface, a side along a direction of projection of UV light, a side proximate to or along the signal source, etc.), any component of the unit 10 including those discussed herein, or any combinations thereof. Some embodiments may include the unit 10 being moved sideways while facing forward at a predefined interval(s), a clock time(s), or a disinfection cycle(s) during operation.

Further, alternately or additionally, the unit 10 may include or be adapted to removably include one or more mechanical components for adapting the unit 10 or a portion thereof to move (e.g., pan, swivel, rotate, tilt, oscillate, pivot, extend, etc.) upon receiving a control signal from a control system, discussed below in greater detail. Examples of the mechanical components may include, but are not limited to, motors, gears, belts, chains, linkages, cams, rollers, wheels, pulleys, levers, springs, ball bearings, or any combinations thereof. The unit 10, or a portion thereof, may be configured to move independently or relative to another portion, object, or stimulus. For example, a portion of the unit 10 may be configured to move about a predetermined axis (e.g., horizontal, vertical, or oblique) relative to the chassis 12 or the cabinet 16. In another example, a portion of the unit 10 may be configured to move about an axis perpendicular to the mobile carriage 14, or any suitable angle ranging from 0 to 90 degrees relative to the mobile carriage 14. For instance, an upper portion, a side portion, and/or a lower portion of the unit 10 including a UV lamp may be configured for being moved gradually after predefined time intervals, e.g., ranging from 5 seconds to 60 seconds, until such movement is complete to a preset angle, or an interim angle, relative to the mobile carriage 14 or the floor. In yet another example, a portion of the unit 10 may be configured to move within or along vertical planes aligned with an outer surface of the chassis 12, the mobile carriage 14, or the cabinet 16. In some other examples, a portion of the unit 10 may be configured to move relative to another portion of the unit 10. For instance, a first half, an upper surface or portion, or a first lateral region of the unit 10 may be configured to move relative to a second half, a lower surface or portion, or a second lateral region respectively of the unit 10. Other examples may include, without limitation, the unit 10, or a portion thereof, being configured to move based on (i) an electrically, magnetically, or optically active marker, or alternatively a passive marker, arranged along a surface, (ii) a predefined path, (iii) a sensor such as those mentioned above, and (iv) signals, or strengths thereof, received from the signal source located either on the unit 10 or proximate thereto.

Embodiments of the unit 10 may include one or more UV lamps. For example, in one embodiment, the unit 10 may include a pulsed xenon UV lamp or head assembly 18 being supported from the chassis 12 by a pair of parallel vertical columns 20 having a pair of parallel horizontal upper and lower stringers 22, 23. The head assembly 18 is secured to a vertical journal 24, which is seated in registered bearing surfaces 25 of the stringers 22. A motor 26, secured to the lower stringer 23, engages a belt drive 28 to selectively rotate the journal 24, and hence, the head assembly 18, in a panning motion about a vertical axis relative to the chassis 12 or the floor.

With reference to FIGS. 4 and 6, it will be seen that the head assembly 18 carries a first UV lamp, e.g., a xenon UV lamp 30 mounted between a front panel 32, having an opening with a fused quartz window 33, preferably without optical filters, and a rear panel 34. The front and rear panels 32, 34 are fixed in parallel relationship by a plurality of spacer rods 36 and a motorized tilt mechanism 38 joins the top of the journal 24 to the head assembly 18. The tilt mechanism 38 rotates about a horizontal axis relative to the chassis 12 for selectively pivoting the head assembly 18 from a retracted position, seated in a recessed portion of the cabinet 16 as illustrated in FIG. 1, to an operative position, shown in FIGS. 2-7a, and vice versa, and may position a head including the xenon lamp 30 at any desired angle there between. The tilt mechanism 38 in combination with the belt driven journal 24 may allow a precise pan, swivel, tilt, and rotate movement of the head assembly 18.

It should also be noted that the head assembly 18 includes a parabolic reflector 40, which reflects the UV light towards the target area. The reflector 40 is mounted directly behind the xenon UV lamp 30, and is fabricated of metal or any suitable material to reflect preferably 95% or more of the light in the UV region of interest suitable for disinfection. Positioning the reflector 40 behind the xenon UV lamp 30 helps direct most of the emitted UV light in the direction of the target, instead of dissipating it at 360-degrees around the entire room and therefore, conserves energy. The beam generated by the lamp/reflector combination may preferably be wide to maximize coverage of a target area instead of being a concentrated beam; however, other suitable lamp/reflector configurations are possible, with more concentrated beams of UV light.

To dissipate the heat generated by the xenon UV lamp 30, an airflow device such as a fan 42 may be positioned at an opening through the rear panel 34 of the head assembly 18 and a heat sink 44 may also be employed. Cooling may be augmented by creating a negative air pressure within the cabinet 16 to draw out the warm air from an area around the xenon UV lamp 30 as well as any heat generated by the control electronics and power circuitry carried by the chassis 12. In this regard, another airflow device such as a vacuum pump 46 having a channeling device such as a suction hose 48, which extends to the rear panel 34, assures that air flow from the head assembly 18 will exhaust through louvered vent openings 35 in the cabinet 16. One or more auxiliary blowers may also be employed to expel warm air out of the vent openings 35, with optional filtration of the exhaust.

A video camera 50, mounted in the front panel 32, is employed to remotely monitor the targeted surface disinfection system in operation and for remotely moving the unit 10, or any component thereof, for disinfection of different target areas within the same room. The movement of the mobile platform 14 and the entire operation of the system may be remotely controlled by an operator (e.g., located at a safe distance, outside the room being disinfected with UV) via a handheld smart device (such as a tablet, etc.) wirelessly connected to a wireless hub and to a control unit 60 fitted within the chassis 12. An operator standing outside the room also has the ability, on his or her tablet, to watch the targeted surface disinfection system in operation through a live-streaming of target areas using the video camera 50 and can also cause the unit 10 to move within the room using a virtual joy stick provided on the tablet's screen, or a tangible joy stick connected physically or wirelessly to the tablet.

The cabinet 16 encloses an electrical power supply and control system for the mobile carriage or platform 14, the xenon UV lamp 30, or any other component in communication with the unit 10. An external power cord (not shown) is plugged into a suitable electrical outlet in the room for powering the unit 10. The power cord may be stored on a retractable reel disposed inside the cabinet 16.

Pursuant to the present invention, a high voltage power supply 52, for energizing the xenon UV lamp 30, is mounted in the chassis 12. A pulse configuration control unit comprising programmable pulse configuration pc boards is positioned in a control card box 54 which is mounted to the chassis 12. Also carried by the chassis 12 is a wireless router or hub 56 for data transfer and communication links with a remote operator and server, a regulated dc power supply 58, a central control unit 60 having an RF transmitter for communication with a door card and programmable motor controller cards 62 for controlling the motor 26 and a motor of the tilt mechanism 38, effecting articulation of the head assembly 18 as well as a motor or motors of the mobile carriage or platform 14. The control card box 54, the central control unit 60 and the motor controller cards 62 will hereinafter collectively be referred to as the "control system".

In another embodiment, shown in FIG. 7b, the unit 10 may include the second lamp or head assembly 102 ("lamp assembly 102") in combination with the lamp or head assembly 18. FIGS. 7b-7e illustrate only components necessary to implement the lamp assembly 102 with the unit 10 for the sake of brevity. One having skill in the art would be able to implement any additional structural or functional aspects including those described in the heretofore based on the concepts discussed herein. In some embodiments, the lamp assembly 102 may be adapted to operate independently, or in combination with the head assembly 18, to support one or more germicidal lamps. The lamp assembly 102 may be supported by the chassis 12; however, some embodiments may include the entirety or aspects of the lamp assembly 102 being supported by the cabinet 16 or the head assembly 18. The lamp assembly 102 may include a lamp housing 104, a second UV lamp 106, and a frame 108 being supported on a movable support assembly coupled with the unit 10. The movable support assembly may include a movable support 110 being coupled to the chassis 12. The movable support 110 may include a fixed portion permanently connected or formed integral with the chassis 12 using any of a variety of connection mechanisms known in the art. Examples of these connection mechanisms include, but are not limited to, welding, molding, a snap fit, a screw fit, a luer-lock, and gluing, which may be chosen depending on the materials from which the fixed portion and the chassis 12 may be made. The movable support 110 may also include a movable portion configured to move (e.g., pan, swivel, rotate, tilt, pivot, extend, etc.) using any suitable movable joint (not shown) known in the art, about a vertical axis X-X' perpendicular to the floor or aspects of the unit 10 such as the mobile carriage or platform 14, and/or xenon UV lamp 30. In some embodiments, the movable joint may be coupled to a motor (not shown) for driving the lamp assembly 102 or the movable portion included therein about the vertical axis X-X' at predefined intervals as intended. In some embodiments, the vertical axis X-X' may be parallel to the chassis 12 or the head assembly 18. Other embodiments may include the movable portion of the support 110 being configured to move sideways while the lamp housing 104, or the second UV lamp 106 arranged therewith, may be facing forward relative to predetermined aspects, components, positions, and/or orientations such as those described above for the unit 10. The movable portion of the support 110 may be coupled with the frame 108 configured to movably support the lamp housing 104.

The frame 108 may be coupled to the movable portion at a predefined length depending on (i) an amount of load (e.g., exerted by the second UV lamp 106 or the lamp housing 104) carried by the support 110, (ii) an amount of torque required for rotating the support 110, (iii) a number and positioning of electrical wires and/or hoses (e.g., cooling hoses), and (iv) positioning of the lamp housing 104 or the second UV lamp 106 relative to the cabinet 16 or any modification thereof adapted to fully, or partially, enclose only the lamp assembly 102, the lamp housing 104, or the entire unit 10 including the lamp assembly 102.

The frame 108 may include a base 112 and a set of one or more arms such as a first arm 114-1 and a second arm 114-2 (collectively, arms 114) extending therefrom. As shown in the illustrated embodiment, the base 112 may be rotatably coupled to the movable portion of the support 110; however, some embodiments may include the base 112 being rotatably coupled to the fixed portion of the support 110. The base 112 may be configured to rotate about a vertical axis Y-Y' relative to the frame 108. For example, the vertical axis Y-Y' may extend along a center of the frame 108. In another example, the vertical axis Y-Y' may extend along a lateral surface, or a portion proximate thereto, of the frame 108.

The arms 114 may extend perpendicular to the base 112; however, other suitable acute or obtuse angles, or combinational sub-branches thereof, relative to the base 112 may be contemplated adapted to provide stability to the frame 108 and the lamp housing 104 during operation. The first arm 114-1 may have a first inner surface including a portion of a channeling device or portion ("channeling portion") extending therethrough. In one example, the channeling portion may include a bifurcated portion of the suction hose 48, while another portion may also extend to the head assembly 18 and have an opening proximate to the xenon UV lamp 30. In another example, the channeling portion may include, coupled or integrated with a separate suction hose (not shown) in flow connection with the vacuum pump 46 and/or any other airflow device. Other examples may include the channeling portion being an air path created by a portion of the lamp housing 104, the frame 108, the chassis 12, the head assembly 18, the cabinet 16, or any combinations thereof.

On the other hand, the second arm 114-2 may have a second inner surface to which the second UV lamp 106 may be secured. However, in some embodiments, the second UV lamp 106 may be secured with the lamp housing 104. The first inner surface may be located opposite, e.g., axially opposite, to the second inner surface and have a predefined distance ("arm separation") therebetween. The arm separation may be sufficient to stably align the lamp housing 104, or a portion thereof, with the frame 108, e.g., between the arms 114. In some embodiments, the arm separation may be defined by a length or curvature of a portion of the frame 108.

The lamp housing 104 may be adapted to fully, or partially, receive and/or support the second UV lamp 106. The lamp housing 104 may be movably coupled to the frame 108 using any of a variety of mechanical components and mechanisms such as those mentioned above. In one embodiment, the lamp housing 104 may include one or more side openings (not shown) for being mounted with the frame 108. For example, the lamp housing 104 may include a first side opening (not shown) and a second side opening (not shown) for being arranged adjacent to the first arm 114-1 and the second arm 114-2 respectively. The first side opening may be configured to receive the channeling portion such as a portion of the suction hose 48 ("hose portion 48") extending from the first inner surface, and the second side opening may be configured to receive the second UV lamp 106 secured to the second inner surface of the frame 108. Upon being received, the hose portion 48 may have a hose opening 116 arranged proximate to the second UV lamp 106 in various configurations to remove warm air around the second UV lamp 106. For example, the received hose portion 48 or the hose opening 116, and the second UV lamp 106 may be arranged along the same axis such as a horizontal axis, a vertical axis, and an angular axis. In another example, the received hose portion 48 or the hose opening 116, and the second UV lamp 106 may be arranged parallel to each other or located in the same plane. In yet another example, the received hose portion 48 or the hose opening 116, and the second UV lamp 106 may be arranged either non-parallel to each other or located in different planes. In still another example, the received hose portion 48 or the hose opening 116 may be located vertically offset from the second UV lamp 106. In some embodiments, the lamp housing 104 may be detachable from the lamp assembly 102, or a component thereof such as the frame 108 and/or a portion of the movable support 110.

The channeling portion may extend from the lamp assembly 102 to the chassis 12. For example, as illustrated in FIG. 7c, the hose portion 48 may be routed from within a hollow body of the support 110 to the chassis 12. In another example, the hose portion 48 may be routed to the chassis 12 along the frame 108 and/or the support 110. Other examples may include the hose portion 48 being routed towards the head assembly 18, or the xenon UV lamp 30 carried therewith, and/or the cabinet 16. The hose portion 48 from the lamp assembly 102 may be fluidically coupled to the vacuum pump 46 or any other suitable airflow device for creating an airflow away from the lamp housing 104, or the second UV lamp 106 arranged therewith, to expel the warm air therefrom.

The channeling portion or the hose portion 48 may further include an exhaust portion (not shown) configured to expel air from the lamp housing 104. The exhaust portion may include an exhaust opening (not shown) to discharge the warm air therethrough received from the lamp housing 104. In some embodiments, aspects of the hose portion 48, the hose opening 116, the exhaust portion, and/or the exhaust opening may include or be replaced with an air path, and an air outlet connected thereto, created by portions of the unit 10, the cabinet 16, or any modifications thereof.

One or more embodiments may include the air path, the air outlet, the exhaust portion, and/or the exhaust opening being configured to direct the air, or a portion thereof, from the lamp housing 104 towards an ambient surrounding or a predetermined portion of the unit 10. Aspects of the air path, the air outlet, the exhaust portion, and/or the exhaust opening may be aligned with louvered vent openings in the cabinet 16, or modifications thereof, to exhaust the warm air. However, in some embodiments, the air path, the air outlet, the exhaust portion and/or the exhaust opening may be aligned along the lamp assembly 102 or a component thereof such as the lamp housing 104. In some other embodiments, the air path, the air outlet, the exhaust portion and/or the exhaust opening may be aligned along, below, or above the head assembly 18 and/or the lamp assembly 102. In still other embodiments, the air path, the air outlet, the exhaust portion and/or the exhaust opening may be aligned along a side surface, an upper portion, a lower portion, or a bottom surface of the chassis 12. Other embodiments may include the air path, the air outlet, the exhaust portion and/or the exhaust opening being aligned along the xenon UV lamp 30 and/or the second UV lamp 106. Optionally, the lamp housing 104 may additionally or alternatively include blowers (not shown) to expel the warm air out of the lamp housing 104 via the same or a different air path or an air outlet. In some embodiments, the exhaust opening and/or the air outlet may be fitted with a filter such as a dust filter (e.g., a high-efficiency particulate air (HEPA) filter) and/or a gas filter (e.g., an ozone filter). Other embodiments may include any such filters being located proximate to the air outlet and/or the exhaust opening.

The lamp housing 104 may be rotatably secured to the one or more arms 114 using any of a variety of mechanical components and mechanisms known in the art including those mentioned above. Upon being secured, the lamp housing 104 may be configured to rotate about a horizontal axis relative to the frame 108 or at least one of the arms 114, the lamp assembly 102, the chassis, or any components (e.g., the suction hose 48, the second UV lamp 106, etc.) coupled thereto. For example, the lamp housing 104 may be configured to rotate about a horizontal axis T-T' extending through the second UV lamp 106 and the hose opening 116 proximate thereto. In another example, a portion of the lamp housing 104 may rotate only about the second UV lamp 106. In yet another example, a portion of the lamp housing 104 may rotate only about the hose opening 116 proximate to the second UV lamp 106.

The lamp housing 104 and/or the base 112 may have any suitable configuration known in the art to reduce friction therebetween during rotation. For example, a lower surface of the lamp housing 104 may be elevated from the base 112 or the lamp housing 104 may be suspended above the base 112 upon being secured to the arms 114. In another example, an outer surface of the lamp housing 104 may include rollers (not shown) configured to roll over a surface of the base 112 during rotation. In yet another example, a surface of the base 112 proximate to the lamp housing 104 may include holes (not shown) configured to blow air at a predefined pressure towards the lamp housing 104 during rotation. The holes may be fluidically connected to an airflow device (not shown) either directly or via a hose. The airflow device may be supported or aligned with the frame 108, the chassis 12, the cabinet 16, or any modifications thereof.

Within the lamp housing 104, the second UV lamp 106 may be arranged adjacent to an emission window 118 of the lamp housing 104. The emission window 118 may refer to a portion of the lamp housing 104 including, partially including, or excluding components (e.g., to create an opening) or agents that allow or facilitate a germicidal or an intended portion of a projected light to pass through. Examples of such components may include, but not limited to, a quartz window, an optical filter, or any other optically permissive barrier or enclosure such as a glass. Examples of such agents may include, but not limited to, vapors, mists, smoke, fluids, etc. The second UV lamp 106 may be similar to the xenon UV lamp 30; however, any suitable types of UV lamps known in the art, related art, or developed later including, but not limited to, a mercury-based UV lamp, a continuous UV lamp or a non-pulsed UV lamp, a pulsed UV lamp, a broad-spectrum UV lamp, a narrow-spectrum JV lamp, and a UV light emitting diode (LED) may be implemented. The second UV lamp 106, with or without the xenon UV lamp 30, may assist to irradiate a single target surface or a set of target surfaces for disinfection. Although the lamp assembly 102 is being described with respect to a single UV source, one having skill in the art would understand that multiple light sources including, but not limited to, one or more UV lamps, visible light lamps, and/or infra-red lamps may be arranged with the lamp assembly 102 or the head assembly 18.

The lamp housing 104 may include one or more optical manipulators configured to manipulate (i) a direction of light projection and/or (ii) characteristics (e.g., intensity, power, frequency, etc.) of the UV light incident on a target surface or that emitted by the second UV lamp 106. Examples of the optical manipulators may include, but are not limited to, lenses, optical filters, or any other less-than-optically transparent screens with or without perforations. In one embodiment, the lamp housing 104 may include a reflector 120 for projecting the light, e.g., from the second UV lamp 106, outwards through the emission window 118. The lamp housing 104 may have any suitable shape, size, and/or cross-section depending on those of the number of light sources such as the second UV lamp 106 and/or ancillary components or electronics arranged therewith.

In one embodiment, the lamp housing 104 or the second UV lamp 106 supported therewith may be arranged within or along (i) an outer surface or (ii) a recessed portion (for the head assembly 18) of the cabinet 16, or any modifications thereof, which may fully or partially enclose the lamp assembly 102. In another embodiment, the lamp housing 104 or the second UV lamp 106 supported therewith may be arranged along the head assembly 18 or the xenon UV lamp 30 carried therewith. In yet another embodiment, the lamp housing 104 or the second UV lamp 106 supported therewith may be arranged to move (e.g., pan, swivel, rotate, tilt, oscillate, pivot, extend, etc.) within the vertical planes aligned along an outer surface of the chassis 12, the mobile carriage 14, and/or the cabinet 16, or any modifications thereof. Some embodiments may include aspects of the lamp assembly 102 being automated or configured to move autonomously. For example, the movable portion of the support 110, the frame 108, and/or the lamp housing 104 may include one or more electric motors for rotation. The motors may be controlled by the control system, e.g., remotely, for predefined automated or autonomous movements of the lamp assembly 102, or components thereof (e.g., the movable portion of the support 110, the frame 108, the lamp housing 104, and/or the second UV lamp 106), relative to the unit 10.

The lamp housing 104 may be configured to be arranged have an outward orientation and an inward orientation. As illustrated in FIG. 7d, in the outward orientation, the lamp housing 104 may be configured to project the UV light substantially exterior to the unit 10. Some embodiments may include the lamp housing 104 being oriented to allow the UV light being partially projected towards an interior of the unit 10 in the outward orientation. In the inward orientation (FIG. 7e), the lamp housing 104 may be configured to project the UV light substantially towards an interior portion of the unit 10. For example, the lamp housing 104 may be configured to project the UV light from the second UV lamp 106 towards a portion within an outer surface of the chassis 12. In another example, the lamp housing 104 may be arranged to project the UV light below the head assembly 18 or a portion of the vertical journal 24, or above the mobile carriage 14. Some embodiments may include the lamp housing 104 being oriented to allow the UV light being partially projected exterior of the unit 10 in the inward orientation. The lamp housing 104 may be rotated about the horizontal axis T-T' either manually, or automatically by the control system, for being arranged in these orientations. In some embodiments, the lamp housing 104 may be rotated in combination with the frame 108 and/or the movable portion of the support 110, or movements thereof. Other embodiments may include the lamp assembly 102 or any component thereof such as the lamp housing 104 being moved in combination or relative to the head assembly 18.

In a third embodiment, as illustrated in FIG. 7f, the unit 10 may include a detachable lamp assembly 202 alone or in combination with the head assembly 18 and/or the lamp assembly 102. The detachable lamp assembly 202 may be similar to the lamp assembly 102 but can be detachably secured with the unit 10. The detachable lamp assembly 202 may include a third UV lamp 204 and a movable support 210 for being detachably secured to the unit 10. The third UV lamp 204 may be supported with a lamp housing 206 movably secured to a frame 208, which may be configured to rotate about the movable support 210. The lamp housing 206, the frame 208, and the movable support 210 may be configured to move (e.g., pan, swivel, rotate, tilt, oscillate, pivot, extend, etc.) in a manner and along relative axes as described above for the lamp housing 104, the frame 108, and the movable support 110 respectively. For example, the lamp housing 206 may be configured to rotate about a predefined axis such as a horizontal axis, a vertical axis, and/or an oblique axis relative to the frame 208 or the movable support 210. In another example, the frame 208 may be configured to rotate about a vertical axis extending along a portion of the movable support 210. The lamp housing 206 may also include any suitable optical manipulator such as those mentioned above. For example, the lamp housing 206 may include a reflector 220 placed proximate to (e.g., behind) the third UV lamp 204 or an emission window of the lamp housing 206.

The movable support 210 may be detachably secured with the chassis 12 using any of a variety of mechanical components and mechanisms known in the art including those described above. For example, a portion of the movable support 210 may be secured with the chassis 12 using a connector 212 attached therewith. The connector 212 may be configured as an interface between the detachable lamp assembly 202 and the unit 10/chassis 12. For instance, the connector 212 may be permanently connected, detachably coupled, or formed integral with the chassis 12 and configured to secure a portion of the movable support 210 using any of a variety of connection mechanisms known in the art. Examples of these connection mechanisms include, but are not limited to, a snap fit, a screw fit, a luer-lock, and friction fit, which may be chosen depending on the materials from which the portion and the chassis 12 may be made.

The connector 212 may include or being coupled with one or more electrical contacts configured to power the detachable lamp assembly 202 or a component thereof (e.g., the third UV lamp 204) upon being secured with the connector 212. The electrical contacts may be electrically coupled with the control and electronics of the unit 10 or any additional components (e.g., batteries) as required. For example, the electrical contacts may be coupled with one or more of the high voltage power supply 52, the hub 56, the regulated dc power supply 58, and the control system similar to the lamp assembly 102 and the xenon UV lamp 30. However, in some embodiments, the detachable lamp assembly 202 may be powered by or include a separate power supply (e.g., a portable battery) and control electronics. One having skill in the art would understand that the movable support 210 of the detachable lamp assembly 202 may be configured with any suitable electrical connectors for engaging with the electrical contacts of the connector 212. However, some embodiments may additionally or alternatively include the electrical connectors being arranged with any other portion or component of the detachable lamp assembly 202 such as the lamp housing 206 and/or the frame 208. The connector 212 may also include or being coupled with a channeling portion or device of the unit 10 (or "unit fluid channeler") configured to couple with a fluid connector of the detachable lamp assembly 202. In one example, the unit fluid channeler (not shown) may include or be in flow communication with a portion of the suction hose 48 or any other component coupled with the vacuum pump 46. In another example, the unit fluid channeler may be a separate hose or a portion/component of the unit 10 in flow communication with an airflow device on the unit 10. The unit fluid channeler may also be fluidically connected directly with the louvered vent openings in the cabinet 16, or modifications thereof, and/or via the air path, the air outlet, the exhaust portion, and/or the exhaust opening associated with the suction hose 48. In some embodiments, the unit fluid channeler may be located on the unit 10 separately from the connector 212.

Further, the detachable lamp assembly 202 may include a channeling device or portion for systemic cooling during operation. For example, the detachable lamp assembly 202 may include a fluid connector such as a hose 214 extending between the lamp housing 206 and the movable support 210. The hose 214 may have a first opening 216 proximate to the third UV lamp 204 and a second opening 218 for communicating with the unit fluid channeler coupled with an airflow device of the unit 10. For instance, a portion of the hose 212 including the second opening 218 may be removably secured with the unit fluid channeler using any of a variety of connection mechanisms known in the art such as those mentioned above including friction fit. Upon being secured, the unit fluid channeler coupled with the airflow device such as the vacuum pump 46 may create a negative air pressure within the lamp housing 206 via the hose 214 and openings 216, 218 thereof, thereby drawing out warm air proximate to the third UV lamp 204. The drawn warm air may be expelled from the louvered vent openings in the cabinet 16 either directly or via the air outlet and/or the exhaust opening associated with the suction hose 48. In some embodiments, the air outlet and/or the exhaust opening may be fitted with a filter such as a dust filter (e.g., a HEPA filter) and/or a gas filter (e.g., an ozone filter). Other embodiments may include any such filters being located proximate to the air outlet and/or the exhaust opening.

Some embodiments may include an airflow device being located on the detachable lamp assembly 202 and configured to expel warm air proximate to the germicidal lamps including the xenon UV lamp 30, the second UV lamp 106, and/or the third UV lamp 204. For example, the lamp housing 206 may include an airflow device and an exhaust opening. This airflow device may be configured to expel warm air proximate to a predetermined germicidal lamp through the exhaust opening, e.g., using the hose 48 and the unit fluid channeler. One having skill in the art would understand to implement any of the required or additional openings, channels, components, and connections with the detachable lamp assembly 202 for removing the warm air therethrough based on the concepts described in the present invention.

In a fourth embodiment, the unit 10 may additionally or alternatively include one or more UV lamps removably supported with the cabinet 16. For example, a removable UV lamp or any ancillary portions thereof, may be integrated with or formed out of a portion of the cabinet 16. In another example, a removable UV lamp may be operatively coupled to a portion of the cabinet 16. For instance, the removable UV lamp may be rotatably mounted with or aligned along a portion of the cabinet 16 or a channel therein (e.g., the recessed portion of the cabinet 16). The removable UV lamp may be configured to rotate upon being engaged with the cabinet 16 in a manner described above for the lamp housing 104 of the lamp assembly 102.

The removable UV lamp may be similar to the xenon UV lamp 30; however, any suitable types of UV sources may be implemented such as those discussed above. The removable UV lamp may be aligned with one or more predefined cavities (not shown) in a cabinet such as the cabinet 16, or any modifications thereof. Each cavity may be adapted for receiving and/or supporting the removable UV lamp, or any structural elements associated therewith. Examples of these structural elements may include, but are not limited to, a cover, wires, ducts, air passages, reflectors, securing or driving mechanisms similar to the lamp assembly 102, portable power sources and other electronics, and so on. Some embodiments may include the cavities being created by a set of one or more removable parts configured for being detachably coupled with the unit 10 or any component thereof including, but not limited to, cabinet 16, the chassis 12, the mobile carriage 14, and/or the head assembly 18.

The number and positions of the cavities may be defined based on a variety of factors including, but not limited to, (i) an intended position of the removable UV lamp relative to the cabinet 16, or the chassis 12, direction of projection, and/or coverage span of the germicidal UV light projected therefrom, (ii) spatial locations of target surfaces relative to (a) distances between the target surfaces, (b) dimensions and structural ability of the unit 10, and/or (c) aspects of the room in which the unit 10 may be placed, (iii) movability of the unit 10, or a portion thereof (e.g., the head assembly 18, the reflectors, the xenon UV lamp 30, the lamp assembly 102, the second UV lamp 106, the third UV lamp 204, etc.), (iv) a rate of disinfection of the target surfaces, (v) a rate of projection, intensity, dose, and/or frequency of UV light emitted from the removable UV lamp alone or in combination with that from the xenon UV lamp 30 and/or the second UV lamp 106 during operation. For instance, the cavities, or the one or more removable UV lamps arranged therewith, may be positioned along an upper portion, a mid-portion, and/or a lower portion of the chassis 12. However, other suitable positions on the unit 10 may be contemplated. Examples of these positions may include, but are not limited to, (i) proximate to the head assembly 18, the xenon UV lamp 30, the lamp assembly 102, or the second UV lamp 106, (ii) proximate to the floor, e.g., along a plane perpendicular or parallel to the floor, (iii) along an outer surface of the mobile carriage 14, (iv) along an exterior surface or interior surface of the cabinet 16, (v) within or along the vertical planes aligned with an outer surface of the chassis 12 or the cabinet 14, (vi) below the head assembly 18 and/or the xenon UV lamp 30 supported therewith, or the lamp assembly 102 and/or the second UV lamp 106 supported therewith, (vii) along or below the vertical journal 24, (viii) proximate to the exhaust opening, the air outlet, or a portion thereof, (ix) proximate to a filter such as the ozone filter, e.g., along the air path or the exhaust portion of the suction hose 48 extending to the filter, and (x) along a cooling system (e.g., the fan, the vacuum pump 46, or any hose or air path fluidically connected thereto or proximate to an outer surface of the cabinet 16, etc.) for the xenon UV lamp 30, the second UV lamp 106, the third UV lamp 204, the removable UV lamp, and/or the operational components such as the power supply 52, 58, batteries, the pulse configuration control unit, the control unit 60, and so on.

Referring now to FIG. 8, wherein components of the high voltage power supply 52 are depicted and may be located within a housing such as the cabinet 16, energy is stored in a high power capacitor 64 for a relatively long period, e.g. a fraction of a second, from which it is released with a shorter time, e.g. nanoseconds to milliseconds, resulting in intense pulses of light generated by the xenon lamp 30, the second UV lamp 106, the third UV lamp 204, and/or the removable UV lamps focused on the target treatment area.

Also included in the housing is a transformer 68, is a capacitor bank 65, inductors 66, a resistor 70, and a cooling fan 72.

An LCD screen 76, fitted with touch screen capability or other input controls, is mounted at the rear of the cabinet 16, enables an administrator to review and interface with the operating parameters and to manually control/adjust/program various operating parameters, such as: the frequency of the UV pulse, the duration of the flashing cycle and to toggle between various modes of flash, etc. The LCD screen graphical interface preferably has capability for being password protected or implements other credential-based login systems that only allow authorized personnel to operate it for programming, repair or diagnostics.

One or more access panels (not shown) on the cabinet 16 allow access to all components (e.g., motors, servos, electronics, robotics, structural members, blowers, etc.) disposed inside the cabinet 16, for assembly and maintenance purposes. In some embodiments, the one or more cavities aligned with the cabinet 16 may define or facilitate implementation of the access panels. Various storage slots and holders can be optionally fitted on or in the cabinet 16 to hold or store various attachments, such as the remote control tablet, various auxiliary safety devices, e.g., emergency shut-off switches, both wireless and manual, may also be located at convenient positions along or within the cabinet 16 or may be stored in pull out trays 74.

The cabinet 16, or any modifications thereof, may also include a handle 78, illustrated in FIG. 1, enabling an operator to manually maneuver the unit 10 from room to room.

The operator located outside the room being disinfected has the ability, on his or her tablet, to remotely pan, swivel and tilt the head assembly 18 in order to precisely direct the UV beam to the area targeted for disinfection. By being able to be positioned close to the target area, no matter how small such target area is, and to treat that area with a concentrated beam of UV light, the unit 10 of the present invention is uniquely suited for spot disinfection of high-touch surfaces in rooms, hospitals, nursing homes and other places.

When not in operation for UV disinfection, the head assembly 18 retracts or folds inside a recess provided in the upper section of the cabinet 16. With the head assembly 18 tucked in its retracted configuration, the entire unit 10 is more maneuverable and easier to move around, and the fragile components, especially the xenon UV flash lamp 30 in the head assembly 18, are more protected during moving, transport and storage. In some embodiments, the second UV lamp 106, the third UV lamp 204, and/or the one or more additional removable UV lamps may be activated when the head assembly 18 may be retracted. The second UV lamp 106 may be arranged in the inward orientation to project the UV light towards a predetermined portion of the unit 10 such as a storage or stowing unit within vertical planes aligned along an outer surface of the chassis 12 or the cabinet 16.

If ozone by-production by the UV flash lamp such as the xenon UV lamp 30, the second UV lamp 106, and the third UV lamp 204 is a concern, which might only be expected at high lamp power levels, the same cooling system can be optionally adapted to also remove the ozone by-product, by fitting ozone filters within the path of the cooling air stream exhausted by the vacuum pump 46. Normal dust air filters can also be optionally fitted. The air stream drawn from the head assembly 18, the additional lamp assembly 102, and/or the detachable lamp assembly 202, may also be employed to cool the control electronics mounted to the chassis 12.

In one embodiment, the xenon UV flash lamp 30, the second UV lamp 106, the third UV lamp 204, and/or the additional removable UV lamps can comprise a commercially available xenon UV flash lamp which, pursuant to the present invention, is programmed to simultaneously emit 30-150 joules of energy per pulse at a frequency of 20-50 Hz, with a further preferred pulse rate of 25-35 Hz. At a pulse rate above 25-30 Hz, the visible flicker of the emitted visible light is almost un-noticeable, appearing as a quasi-continuous light with no annoying pulsing-flash effect. Also, such UV pulse rates above 25-30 Hz, with the relatively low 30-150 joules of power per pulse, as employed in the present invention, produce a much softer, gentle humming sound during operation, avoiding the annoying loud popping/cracking sound commonly generated by prior art pulsed UV systems operating at lower pulsing rates and higher levels of power per pulse, such as, the prior art systems referenced above, which operate below 2 Hz and above 500 joules of power per pulse. The much softer sound generated by the operation of the present invention greatly reduces the discomfort and disturbance caused to people, often hospital patients, located in the vicinity of the room being disinfected.

In another embodiment, the xenon UV lamp 30 may be configured to operate in combination with another light source to emit energy at a combined frequency of greater than 2 Hz. For instance, the xenon UV lamp 30 may be operated in combination with the second UV lamp 106, the third UV lamp 204, and/or the additional removable UV lamps to emit a predefined amount of energy, e.g., 30-150 joules per pulse, at a combined frequency of 20-50 Hz. One example may include the xenon UV lamp 30 being configured to emit UV light at a frequency of 15 Hz while the second UV lamp 106 may be made to emit UV light at 5 pulses per second, thereby projecting a predefined amount of UV light on to one or more target surface(s) at a combined UV frequency of 20 Hz. Another example may include the xenon UV lamp 30, the second UV lamp 106, and a removable UV lamp being configured to emit the UV light at frequencies of 30 Hz, 10 Hz, and 5 Hz respectively to project the combined UV light at a combined frequency of 45 Hz. Yet another example may include the xenon UV lamp being configured to emit UV light at a frequency of 5 Hz while the removable UV lamp may be made to emit UV light at 30 pulses per second, thereby projecting a predefined amount of UV light at a combined UV frequency of 35 Hz. Still another example may include the xenon UV lamp 30, the second UV lamp 106, the third UV lamp 204, and a removable UV lamp being configured to emit the UV light at frequencies of 5 Hz, 10 Hz, 15 Hz, and 20 Hz respectively to project the combined UV light at a combined frequency of 50 Hz. One having skill in the art would be able to contemplate other suitable combinations of frequencies for the germicidal lamps associated with the unit 10. Such a distributed frequency configuration may assist for (i) an efficient power distribution to the unit 10 and each of the lamps operating therewith, (ii) interruption-free disinfection cycles, and (iii) target-based (or pathogen-based) emission of UV energy.

Another aspect of the present invention is a software system, which may combine, among other functions, a control function (local and remote), a billing/record keeping function, a safety function, a scan the area to be treated function and a lamp life/output monitoring function. Using various sensors and hardware control units, the software system can, for example, track exactly the number and the energy of all UV pulses delivered during the life of a particular unit or lamp or during any particular cleaning step, thus enabling a bill by the number of UV pulses invoicing framework for the operation of the unit 10.

The wireless communication router or hub 56, using any suitable wireless protocol, is included as part of the hardware and software of this invention, allowing bi-directional communication with a wide range of remote accessories, sensors and controls.

In conjunction with optional remote or wired sensors, such as, door cards, motion sensors, occupancy sensors, temperature sensors, smoke sensors, ozone sensors, etc., the software can also implement an operational safety regime for the entire system, whereby the unit 10 shuts down automatically if any dangerous conditions are encountered or detected by the remote sensors, e.g. motion/vibration detected proximate to the unit 10 or at a door of the room being disinfected, signifying that a person is about to enter the room while the unit 10 is operating, etc.

The software system may consist of different modules, e.g., the control system (central control unit 60, the motor control card 62 and the control cards box 54, located on the chassis 12 or any connected hardware), other modules which may be located on a remote web server, and some of which are installed on a tablet, or other smart handheld device. An operator will preferentially use the tablet as the main remote user interface. The tablet positioned outside the room being disinfected communicates wirelessly, via any suitable wireless protocol such as WiFi, Bluetooth, RF, etc., with the communication hub 56 and the control system. The same tablet may also communicate, via a cellular data connection, e.g., GSM, 3G, LTE, etc., with a remote web server where some of the software functionality of this invention may be implemented, such as, tracking, billing, auditing, performance monitoring, record keeping, etc.

An optional GPS module on the tablet can relay to the remote webserver the precise location where each UV disinfection unit such as the unit 10 is deployed, enabling the remote webserver to offer centralized background processing and database services for a large number of UV disinfection units field-deployed anywhere in the world.

Typical Mode and Method of Operation for a Preferred Embodiment

In an exemplary mode and method of operation, an embodiment of this invention is used to disinfect the high touch surfaces in a hospital room, a typical source of germs, which cause hospital acquired infections. The functional strength of this invention is for targeted surface disinfection of relatively smaller areas, as opposed to the whole room disinfection at once approach of the prior art systems. Indeed, objects such as equipment and furniture in a room being disinfected make one shot whole room disinfection almost impossible.

Typically, the targeted surface disinfection unit 10 is wheeled into a room which contains the target area to be disinfected by UV light. However, in some embodiments, the unit 10 or any of the germicidal lamps (e.g., the xenon UV lamp 10, the second UV lamp 106, the third UV lamp 204, etc.) connected therewith may be positioned proximate to the room or the target area for being disinfected. After orienting the unit 10, or a germicidal lamp connected therewith, toward the general target area and plugging in the unit's power cord into a wall AC power outlet, the operator leaves the room, places a motion sensing tag, e.g., a door card, at the entrance door, and remotely initiates a disinfection cycle from the tablet.

At the beginning of a UV disinfection cycle, the unit's head assembly 18 moves into its normal upright operating position, illustrated in FIGS. 2-3 by tilting up from of its stored folded down position, illustrated in FIG. 1. In tandem with the head assembly 18 or independently, the second UV lamp 106 or the third UV lamp 204 may be moved into a predefined orientation relative to the head assembly 18 and/or the removable lamp based on the target surfaces. For example, the second UV lamp 106 may be arranged fully, or partially, in the inward orientation for disinfecting a target surface or object within or along the cabinet 16 while the third UV lamp 204 may be arranged to project the UV light exterior to the unit 10, or vice versa. Another example may include the second UV lamp 106 being arranged fully, or partially, in the outward orientation for disinfecting a target surface spatially away from (i) a direction of UV emission or (ii) another target surface being disinfected by the xenon UV lamp 30 and/or the third UV lamp 204. A pre-programmed number of UV flashes of a programmed intensity and pulse frequency are then delivered by one or more germicidal lamps such as the xenon lamp 30, the second UV lamp 106, the third UV lamp 204, and/or the removable UV lamps to the one or more target surfaces. Once the UV disinfection cycle has been completed, the motorized tilt mechanism 38 is actuated to tilt the head assembly 18 into its stored position, and the second UV lamp 106, the third UV lamp 204, and/or the removable UV lamps, may be switched-off.

During the UV disinfection process, the door card such as the door card 80 placed on the access door to the room continuously monitors for the detection of any movement at or around the door. Detection of movement or vibration around the door of the room being treated will result in an immediate emergency shut off of the control system, the targeted surface disinfection system or any particular component thereof, e.g., the xenon UV lamp 30, the second UV lamp 106, the third UV lamp 204, and/or the removable UV lamps, etc.

By using a tablet or a handheld smart device on which the control software is installed, the operator can remotely interact with the control system within the chassis 12, can select operational parameters, can initiate or stop all steps involved in the process, and can as well see inside the room by accessing the video camera 50.

An optional first step could consist of an automated scanning of the general target area by the control unit 60, or the operator can select a manual or preprogrammed xenon lamp flashing routine. The xenon lamp 30 is initially positioned perpendicular to the vertical axis and parallel to floor, but the operator can remotely pan, swivel and tilt the head assembly 18 to a predetermined angle relative to the chassis 12, in order to precisely direct the beam of UV light to the targeted surface to be disinfected.

The tablet may be programmed with a virtual joystick to enable the operator to remotely drive, direct and navigate the unit 10 within the room by controlling the motors of the platform 14 so that multiple target surfaces may be disinfected without the need to re-enter the room to re-position the unit 10 after each target surface has been disinfected. In some embodiments, the mobile carriage 14, the chassis 12, or components supported therewith (e.g., the head assembly 18, the lamp assembly 102, the detachable lamp assembly 202, or any parts thereof such as the second UV lamp 106, the third UV lamp 204, the removable lamps, etc.), may be configured to navigate autonomously.

Alternatively, the targeted surface disinfection system may be provided without remote controlled or autonomous robotic navigational capabilities. The principle of operation would be similar, however. After completing the disinfection of one target surface, the operator would reenter the room and manually reposition the unit 10 in front of the next disinfection target surface, exit the room and remotely start the next disinfection cycle.

Various embodiments of this invention, with or without remote controlled or autonomous robotic navigational capabilities can be built with a common chassis 12, the head assembly 18, the lamp assembly 102, and the detachable lamp assembly 202, which could then be fitted either on a non-motorized wheeled platform, or on the motorized robotic the wheeled platform 14. Each platform will have the same component dimensions to accommodate the chassis 12, the head assembly 18, the lamp assembly 102, the detachable lamp assembly 202, and/or the removable UV lamps. This modular construction offers flexibility and ensures that no major changes will be needed for the manufacturing either version of the unit 10. Some embodiments may include any of the lamp assemblies such as the head assembly 18, a second lamp assembly 102, a third detachable lamp assembly 202, and/or the removable UV lamps being positioned on a separate platform(s), which may be structurally or functionally connected, locally or remotely controlled, motorized or non-motorized, wheeled or non-wheeled, and autonomous or non-autonomous.

Preferred Parameters of UV Irradiation

The xenon lamp 30 comprises an electrical U-shaped xenon UV discharge lamp placed behind the clear fused quartz window 33. No region of the emitted radiation is filtered in a preferred embodiment, due to the experimental observation that all regions of emitted radiation, i.e. UV-A, UV-B, UV-C and even the visible region, contribute positively to the disinfection process.

In contrast with the prior art trend of using high powered lamps (with emitted energies above 500 joules per pulse), the inventors herein made the surprising observation that better disinfection results (requiring less UV exposure time for germ inactivation) are achieved with a lower-power xenon UV discharge lamp of a typical emitted energy of 30-150 joules per pulse, by operating at a higher frequency of 20-50 Hz, compared to a frequency of less than 2 Hz used in the prior art. Additionally, in the prior art, energy per pulse varied as a function of frequency. If the frequency was decreased, the energy per pulse increased, and if the frequency was increased, the energy per pulse decreased, whereas pursuant to the invention, for a certain set of conditions the energy per pulse remains constant regardless of pulse frequency variations.

A preferred sub-range of pulse rate for the present invention is 25-35 Hz, with higher rates resulting in increased amperage draw. However, other suitable frequency sub-ranges may be contemplated based on a type, density, and/or disinfection rate of a targeted surface or pathogen. If the unit is to use regular AC wall outlets of the kind normally present in a typical hospital room (120 VAC and 15 A in N. America), the 15 A maximum current draw may become a limit that prevents pulse rates higher than 35-50 Hz from being achievable.

For targeted short-duration disinfection treatments, an alternative embodiment of the present invention may be powered entirely by on-board batteries or other type of rechargeable energy storage devices (e.g., for autonomous movement), without the need to be plugged in to an AC wall-outlet.

As shown in the experimental test values graphed in the FIGS. 9a-9e, the xenon UV discharge lamp can maintain its energy output in the UV region at a reasonably high level, even with a 50 Hz pulse rate.

Further experimental tests performed by the inventors herein show that the presence of a reflector such as the reflector 40 is beneficial for focusing and guiding the bulk of the UV energy output towards the frontal direction of the beam (directly perpendicular to reflector). Experimental data graphed in the FIG. 10 shows how irradiance changes with the angle of the beam, proving that the energy output is much lower at various side angles compared to full frontal direction.

Further experimental data graphed in FIGS. 11A and 11B shows how irradiance towards the target area directly in front of the UV emitter is much greater in the presence of a reflector, proving that the use of a reflector could directly lead to higher energy exposure and shorter exposure times for the same lamp nominal output.

For large rooms and general disinfection, a typical embodiment of the present invention is preferably positioned with the UV emitter at a distance of 10 feet from the target area, which could be covered by the UV beam up to a height of 10 feet in these circumstances; shorter distances are more effective, requiring a lower irradiation time for smaller target areas.

The table below displays experimental results that show a marked decrease of the required disinfection time with an increase of the pulsing frequency for the xenon UV discharge lamp of the present invention. Higher frequency significantly reduces the disinfection time; at 50 Hz (not shown in the table), the disinfection time is in the range of tens of seconds, rather than minutes.

| Frequency | Disinfection time (min) | Disinfection Efficiency |
|---|---|---|
| 5 Hz | 10 | 99.99% |
| 10 Hz | 5 | 99.98% |
| 20 Hz | 3 | 99.99% |
| 30 Hz | 2 | 99.99% |

The table below displays further experimental results showing disinfection efficiency, for UV treatment of MRSA and B. Subtilis with the present invention, to remain higher than 99%, even with reduced exposure times.

| Time (in seconds) | MRSA Efficiency | B. Subtilis Efficiency |
|---|---|---|
| 70 | 99.95% | 97.83% |
| 80 | 99.98% | 99.92% |
| 90 | 99.99% | 99.99% |

Especially when combined with a reduction in the distance between the UV emitter and the target area, the disinfection times can be reduced tremendously and still achieve satisfactory disinfection efficiency, a situation which is uniquely suited for the disinfection of high-touch surfaces in hospital rooms. When placed at a distance of 1 meter from the target area, the present invention achieved a disinfection efficiency of over 99% with very short exposure times, i.e., as little as 10 seconds. This very short disinfection cycle time is unparalleled in the prior art, and allows faster and more efficient disinfection of entire hospital rooms by disinfection of multiple small high-touch surfaces in a rapid succession of cycles using focused UV beams, rather than one very long cycle of disinfecting the entire room with a 360-degree UV beam.

Experimental results reported in the table below indicate the disinfection efficacy of the present invention on various pathogens and the dramatic reduction in disinfection time when the distance between the unit 10 and the target surface is reduced from 10 feet to 5 feet. Indeed with respect to all species tested, the time required for 100% efficiency was reduced by at least one half.

| Species | Time (s) | Distance (ft) | Efficiency | Frequency (Hz) | Power (J) |
|---|---|---|---|---|---|
| B. Subtilis (1) | 60 | 10 | 85.10% | 25-35 | 30-150 |
| B. Subtilis | 120 | 10 | 99.01% | 25-35 | 30-150 |
| B. Subtilis | 180 | 10 | 100.00% | 25-35 | 30-150 |
| B. Subtilis | 30 | 5 | 100.00% | 25-35 | 30-150 |
| B. Subtilis | 60 | 5 | 100.00% | 25-35 | 30-150 |
| B. Subtilis | 120 | 5 | 100.00% | 25-35 | 30-150 |
| MRSA (2) | 60 | 10 | 99.88% | 25-35 | 30-150 |
| MRSA | 120 | 10 | 100.00% | 25-35 | 30-150 |
| MRSA | 180 | 10 | 100.00% | 25-35 | 30-150 |
| MRSA | 30 | 5 | 100.00% | 25-35 | 30-150 |
| MRSA | 60 | 5 | 100.00% | 25-35 | 30-150 |
| MRSA | 120 | 5 | 100.00% | 25-35 | 30-150 |
| VRE (3) | 60 | 10 | 74.94% | 25-35 | 30-150 |
| VRE | 120 | 10 | 95.77% | 25-35 | 30-150 |
| VRE | 180 | 10 | 100.00% | 25-35 | 30-150 |
| VRE | 30 | 5 | 100.00% | 25-35 | 30-150 |
| VRE | 60 | 5 | 100.00% | 25-35 | 30-150 |
| VRE | 120 | 5 | 100.00% | 25-35 | 30-150 |
| c. Diff (4) | 60 | 10 | 98.50% | 25-35 | 30-150 |
| c. Diff | 120 | 10 | 100.00% | 25-35 | 30-150 |
| c. Diff | 180 | 10 | 100.00% | 25-35 | 30-150 |
| c. Diff | 30 | 5 | 98.50% | 25-35 | 30-150 |
| c. Diff | 45 | 5 | 100.00% | 25-35 | 30-150 |
| c. Diff | 50 | 5 | 100.00% | 25-35 | 30-150 |

Species References:
(1) *B. Subtilis* = *Bacillus subtilis*
(2) MRSA = Methicillin-resistant *Staphylococcus aureus*
(3) VRE = Vancomycin-resistant *Enterococci*
(4) *c. Diff.* = *Clostridium difficile*

Door Card Safety Device

Also, the present invention described herein includes a device and system for ensuring safe operation of the UV disinfection unit 10, by preventing humans from being exposed to UV radiation. Embodiments may include the door card 80 being a battery-powered small safety device, meant to be attached to the door of the room being disinfected, by hanging on the doorknob or by any other means, e.g., placing, leaning, etc. Various sensors can be embedded within the door card, e.g., motion sensor, acceleration sensor, shock sensor, IR proximity sensor, photo sensor, etc., to sense or detect movement in the proximity of the door card.

When placed by the door of the room being disinfected, the door card 80 communicates wirelessly with the central control unit 60. During operation, the door card 80 continuously monitors its sensor or sensors for the detection of any movement of the door or proximate the door.

When the unit 10 is operating inside a room, safety requirements mandate that no person could be in that room and the access door to that room must be closed securely. Any movement of an access door could potentially signify that a person is inadvertently attempting to enter the room when it is unsafe to do so; in such a situation, the germicidal lamps such as the xenon UV lamp 30, the second UV lamp 106, the third UV lamp 204, and the removable UV lamps must be turned off immediately.

When movement (or vibration, shock, etc.) is detected above a set threshold on or around a door, the door card 80 transmits a wireless signal which causes the control unit 60 to immediately shut off the germicidal lamps such as the xenon UV lamp 30, the second UV lamp 106, the third UV lamp 204, and the removable UV lamps. After such an emergency shutdown, the UV disinfection operation can only be restarted after the UV disinfection unit 10 and the door card 80 are reset by the operator, and only if the door motion detection state reverts back to normal (no door movement detected).

In a typical embodiment, the door card 80 is powered by a rechargeable battery, has a physical ON/OFF button, is fitted with wireless RF communication, has a 6-axis gyro sensor, and is controlled by an embedded microcontroller chip.

A typical mode of operation for the door card 80 is as follows:

The operator presses the ON/OFF switch, which turns on the microcontroller and central control unit communi-cation;

the microcontroller searches for a hub such as the hub 56 and establishes communication with the central control unit 60;

the microcontroller calibrates itself depending on the position and alignment it currently is (such calibration may take about 20 seconds);

a certain threshold value for the acceleration is pro-grammed within the microcontroller (but it could be changed/reprogrammed with special software);

once calibrated, the microcontroller starts to calculate acceleration in X, Y, Z directions and averages them to establish an overall acceleration;

the microcontroller continuously compares this accelera-tion to a threshold value; as long as this calculated acceleration is below the threshold, the microcontroller sends signals to the central control unit 60 indicating normal status;

when the measured acceleration increases above the threshold value for the first time, the microcontroller starts to monitor further readings to rule out a false alarm;

if the readings are above threshold continuously for a set amount of time, the microcontroller categorizes them as movement and sends a "door movement" signal to the central control unit 60 (which triggers an instant shut down of the germicidal lamps such as the xenon lamp 30, the second UV lamp 106, the third UV lamp 204, and the removable UV lamps), once conditions go return to normal (door not moving), the microcontroller sends "normal" signals to the cen-tral control unit 60.

Thus, it will be seen that there is provided a targeted surface disinfection system with pulsed UV light which achieves the various aspects, features and considerations of the present invention and which is well suited to meet the conditions of practical usage.

In the Figures of this application, in some instances, a plurality of elements may be shown as illustrative of a particular element, and a single element may be shown as illustrative of a plurality of a particular elements. Showing a plurality of a particular element is not intended to imply that a system or method implemented in accordance with the invention must comprise more than one of that element or step, nor is it intended by illustrating a single element that the invention is limited to embodiments having only a single one of that respective element. Those skilled in the art will recognize that the numbers of a particular element shown in a drawing can, in at least some instances, be selected to accommodate the particular user needs.

The particular combinations of elements and features in the above-detailed embodiment are exemplary only the interchanging and substitution of these teachings with other teachings in this and the incorporated-by-reference patents and applications are also expressly contemplated. As those skilled in the art will recognize, variations, modifications, and other implementations of what is described herein can occur to those of ordinary skill in the art without departing from the spirit and the scope of the present invention.

Further, in describing the invention and in illustrating embodiments of the invention in the figures, specific termi-nology, numbers, dimensions, materials, etc., are used for the sake of clarity. However, the present invention is not limited to the specific terms, numbers, dimensions, materi-als, etc. so selected, and each specific term, number, dimen-sion, material, etc., at least includes all technical and func-tional equivalents that operate in a similar manner to accomplish a similar purpose. Use of a given word, phrase, number, dimension, material, language terminology, product brand, etc. is intended to include all grammatical, literal, scientific, technical, and functional equivalents. The termi-nology used herein is for the purpose of description and not limitation.

All publications and references cited herein are expressly incorporated herein by reference in their entirety.

Having described the preferred embodiment of the inven-tion, it will now become apparent to one of ordinary skill in the art that other embodiments incorporating their concepts may be used. Moreover, those of ordinary skill in the art will appreciate that the embodiment of the invention described herein can be modified, to accommodate and/or comply with changes and improvements in the applicable technology and standards referred to herein. For example, the technology can be implemented in many other, different, forms, and in many different environments, and the technology disclosed herein can be used in combination with other technologies. Variations, modifications, and other implementations of what is described herein can occur to those of ordinary skill in the art without departing from the spirit and the scope of the invention.

The particular combinations of elements and features in the above-detailed embodiments are exemplary only the interchanging and substitution of these teachings with other teachings in this and the referenced patents/applications are also expressly contemplated. As those skilled in the art will recognize, variations, modifications, and other implementa-tions of what is described herein can occur to those of ordinary skill in the art without departing from the spirit and the scope of the invention. Accordingly, the foregoing description is by way of example only and is not intended as limiting.

Having thus described the invention, there is claimed as new and desired to be secured by Letters Patent:

1. A targeted surface disinfection system, comprising:
   a motorized articulated assembly carrying a UV source, wherein the motorized articulated assembly includes a journal supported by a chassis;
   a control unit configured for driving the UV source to emit radiant energy upon a target surface requiring disinfec-tion;
   an airflow device located remote from the UV source, the airflow device including at least one of a fan and a vacuum pump, wherein the airflow device is configured to create an airstream for cooling the UV source;
   an air channeling portion extending from proximate the UV source to an exhaust located remote from the UV source, wherein the air channeling portion is a channel defined by a body of an apparatus formed at least in part using the chassis supporting the motorized articulated assembly; and a sensor mounted proximate the UV source or the motorized articulated assembly.

2. The targeted surface disinfection system of claim 1, wherein the vacuum pump creates a negative pressure in the airstream proximate to the UV source, and wherein the air channeling portion includes a hose.

3. The targeted surface disinfection system of claim 1, further comprising an air blower installed proximate to the airstream.

4. The targeted surface disinfection system of claim 1, further comprising an input device mounted along a rear portion of the motorized articulated assembly, the rear portion being located away from a direction of projection of the radiant energy from the UV source, wherein the input device includes a touchscreen configured to receive instructions for adjusting one or more operating parameters of the targeted surface disinfection system.

5. The targeted surface disinfection system of claim 1, wherein the sensor includes a camera.

6. The targeted surface disinfection system of claim 1, further comprising a motor for moving the motorized articulated assembly about a vertical axis or a horizontal axis relative to the chassis.

7. The targeted surface disinfection system of claim 1, wherein the control unit is further programmed for driving the UV source at different frequencies, wherein the UV source emits constant or same radiant energy per pulse at each of the frequencies.

8. The targeted surface disinfection system of claim 1, wherein the control unit is further programmed for driving the UV source to emit a predefined amount of radiant energy for disinfecting the target surface from a distance of at least 1 meter.

9. The targeted surface disinfection system of claim 1, further comprising a mobile carriage for navigating the chassis, wherein at least one of the mobile carriage and the motorized articulated assembly is configured to move autonomously.

10. An apparatus, comprising:

a motorized support including a moveable portion lamp assembly carrying a UV source and a sensor;

a control unit configured for driving the UV source to emit radiant energy upon a target surface requiring disinfection;

an airflow device located remote from the UV source, the airflow device including at least one of a fan and a vacuum pump, wherein the airflow device is configured to create an airstream for cooling the UV source;

an air channeling portion extending-from proximate the UV source to an exhaust located remote from the UV source, wherein the air channeling portion is a channel defined by a body of the apparatus; and a mobile carriage for navigating the apparatus.

11. The apparatus of claim 10, wherein the vacuum pump creates a negative pressure in the airstream proximate to the UV source, and wherein the air channeling portion includes a hose.

12. The apparatus of claim 10, further comprising an air blower installed proximate to the airstream.

13. The apparatus of claim 10, further comprising an input device mounted along a rear portion of the apparatus, the rear portion being located away from a direction of projection of the radiant energy from the UV source, wherein the input device includes a touchscreen configured to receive instructions for adjusting one or more operating parameters of the apparatus.

14. The apparatus of claim 10, wherein the sensor includes a camera.

15. The apparatus of claim 10, further comprising a motor configured to drive the moveable lamp assembly about a vertical axis or a horizontal axis relative to one of a chassis of the apparatus and the target surface.

16. The apparatus of claim 10, wherein at least one of the moveable lamp assembly and the mobile carriage is configured to move autonomously.

17. The apparatus of claim 10, wherein the moveable lamp assembly includes an articulated assembly.

18. The apparatus of claim 10, wherein the control unit is further programmed for driving the UV source at different frequencies, wherein the UV source emits constant or same radiant energy per pulse at each of the frequencies.

19. The apparatus of claim 10, wherein the control unit is further programmed for driving the UV source to emit a predefined amount of radiant energy for disinfecting the target surface from a distance of at least 1 meter.

\* \* \* \* \*